United States Patent [19]

Belloni et al.

[11] Patent Number: 6,034,137
[45] Date of Patent: *Mar. 7, 2000

[54] CATIONIC LIPIDS FOR GENE THERAPY

[75] Inventors: Paula N. Belloni, Half Moon Bay; Donald R. Hirschfeld, Mountain View; John O. Link, San Francisco, all of Calif.; John J. Nestor, Jr., Louisville, Ky.; Gary A. Peltz, Redwood City, Calif.

[73] Assignee: Syntex (U.S.A.) Inc., Palo Alto, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/954,428

[22] Filed: Oct. 20, 1997

Related U.S. Application Data

[60] Provisional application No. 60/029,581, Oct. 22, 1996, and provisional application No. 60/049,922, Jun. 18, 1997.

[51] Int. Cl.⁷ .......................... A61K 31/16; C07C 233/04
[52] U.S. Cl. .......................... 514/626; 514/477; 514/478; 514/546; 514/590; 560/155; 560/157; 560/160; 560/168; 564/34; 564/197; 564/159
[58] Field of Search .................................. 564/197, 159, 564/34; 514/626, 477, 478, 546, 590, 616; 560/155, 168, 157, 160

[56] References Cited

U.S. PATENT DOCUMENTS

| | | |
|---|---|---|
| 3,825,560 | 7/1974 | Saito et al. . |
| 4,271,190 | 6/1981 | Bertelmann et al. . |
| 4,401,594 | 8/1983 | Umezawa et al. . |
| 4,477,428 | 10/1984 | Silbering et al. . |
| 5,141,751 | 8/1992 | Tomikawa et al. . |
| 5,478,946 | 12/1995 | Murad et al. . |
| 5,654,451 | 8/1997 | Kari et al. ................... 554/35 |

FOREIGN PATENT DOCUMENTS

| | | |
|---|---|---|
| 0 125 092 | 11/1984 | European Pat. Off. . |
| 0 125 827 | 11/1984 | European Pat. Off. . |
| 7136604 | 10/1971 | Japan . |
| 60-214768 | 10/1985 | Japan . |
| 8-250489 | 9/1996 | Japan . |
| WO 94/15909 | 7/1994 | WIPO . |
| WO 95/14381 | 6/1995 | WIPO . |
| WO 95/28377 | 10/1995 | WIPO . |
| WO 96/01840 | 1/1996 | WIPO . |
| WO 96/01841 | 1/1996 | WIPO . |
| WO 96/26179 | 8/1996 | WIPO . |

OTHER PUBLICATIONS

Kamino et al, Bull. Chem. Soc. Jpn, vol. 69, 3619–3631, 1996.

Oishi et al, Chem. Commun., pp. 1357–1358, 1997.

Onda, et al., J. American Chemical Society, 1996, vol. 118:36, pp. 8524–8530, "Molecular Recognition of Nucleotides by the Guanidinium Unit at the Surface of Aqueous Micelles and Bilayers. A Comparison of Microscopic and Macroscopic Interfaces".

Ijiro, et al., J. Chem. Soc., Chem. Comm., 1992, vol. 18, pp. 1339–1341, "A DNA–Lipid Complex Soluble in Organic Solvents".

Oishi, et al., Chem. Lett., 1996, vol. 10, pp. 857–858, "Atomic Force Microscopic Observation of Random Molecular Arrangement in Dialkyl Guanidinium Monolayer".

Patent Abstracts of Japan, vol. 097:001 Jan. 31, 1997 and JP 08250489 (Res. Dev. Corp. of Japan), Sep. 27, 1996.

Lewis, et al., Proc. Natl. Acad. Sci., U.S.A., 1996, vol. 93:8, pp. 3176–3181, "A serum–resistant cytofectin for cellular delivery of antisense oligodeoxynucleotides and plasmid DNA".

*Primary Examiner*—Shailendra Kumar
*Attorney, Agent, or Firm*—Rohan Peries

[57] ABSTRACT

This invention provides novel cationic lipids, particularly guanidino lipids, and methods for their preparation. Also provided are polyanionic-lipid complexes comprising the lipids of the invention, their preparation and use to deliver biologically active substances, particularly nucleic acids to cells.

12 Claims, 14 Drawing Sheets

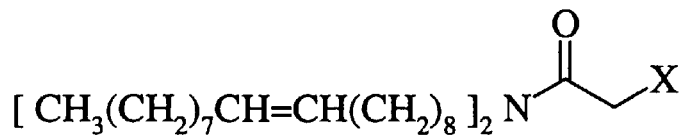
1
2
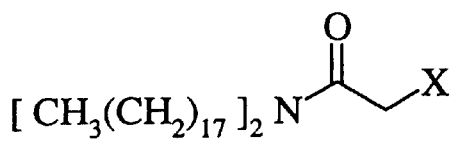
3
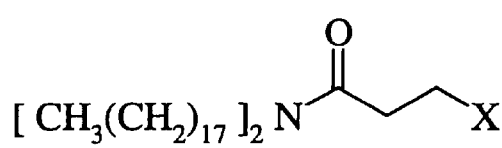
4
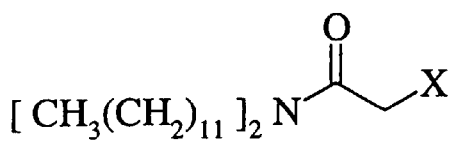
5
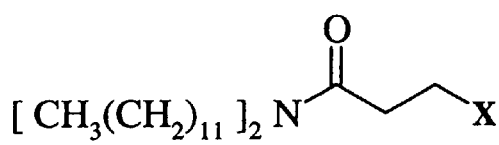
6
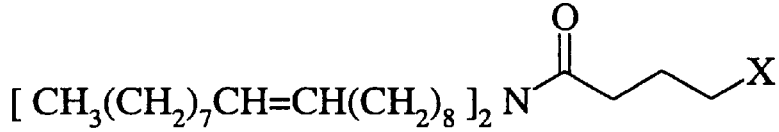
7
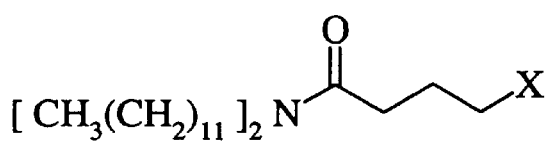
8
FIG._1A

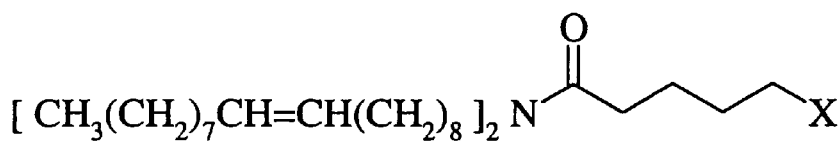
9
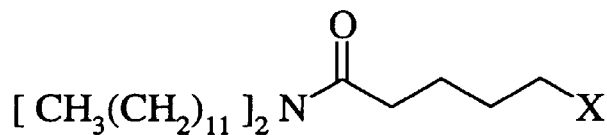
10
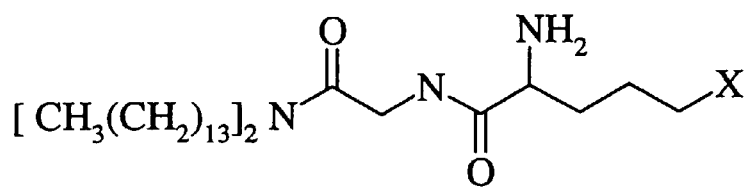
11
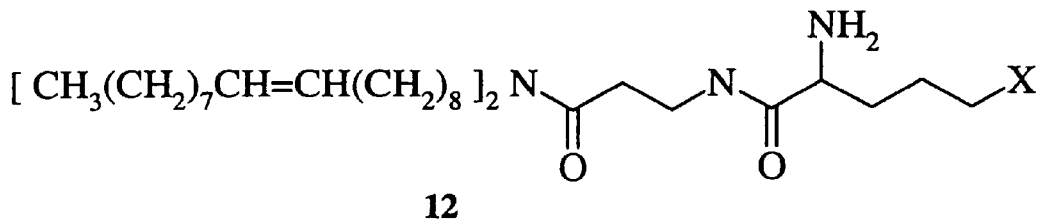
12
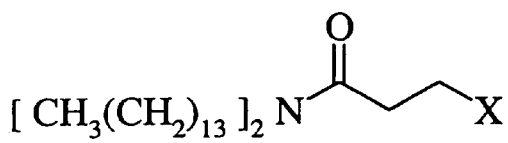
13
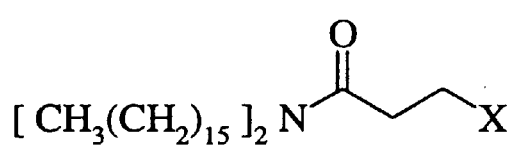
14
FIG._1B X =
 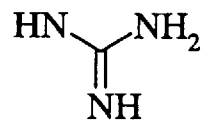 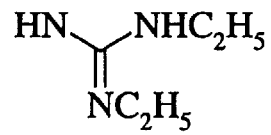 
A    B    C    D
 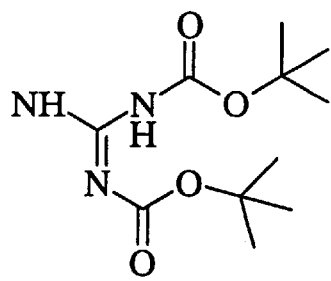 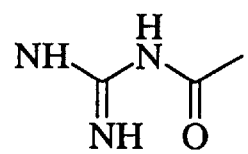
E    F    G
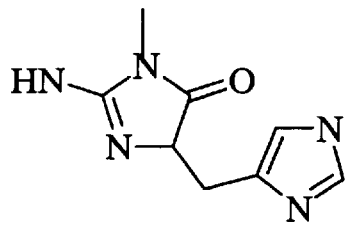 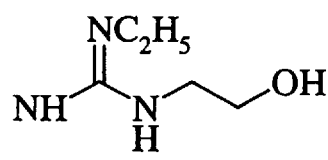 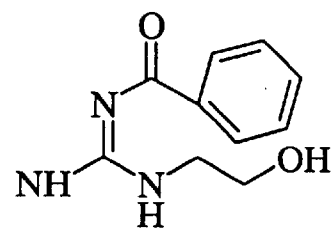
H    I    J
*FIG._2A*

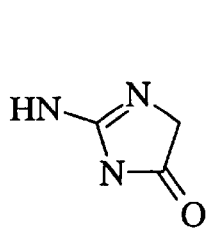
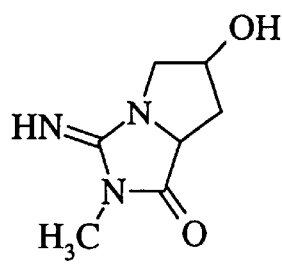
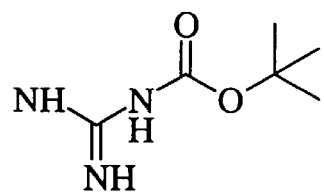
K  M  N
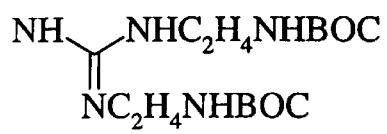
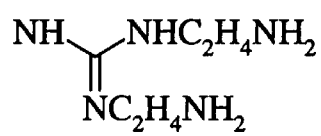
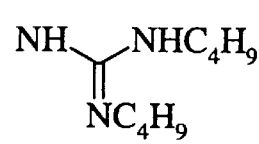
O  P  Q
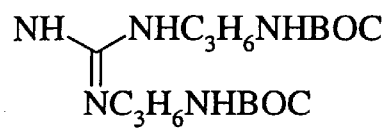
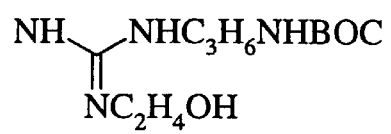
R  S
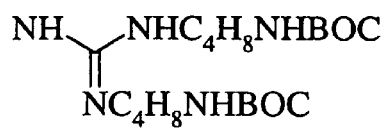
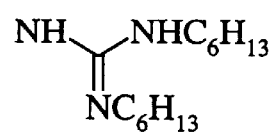
T  U
FIG._2B

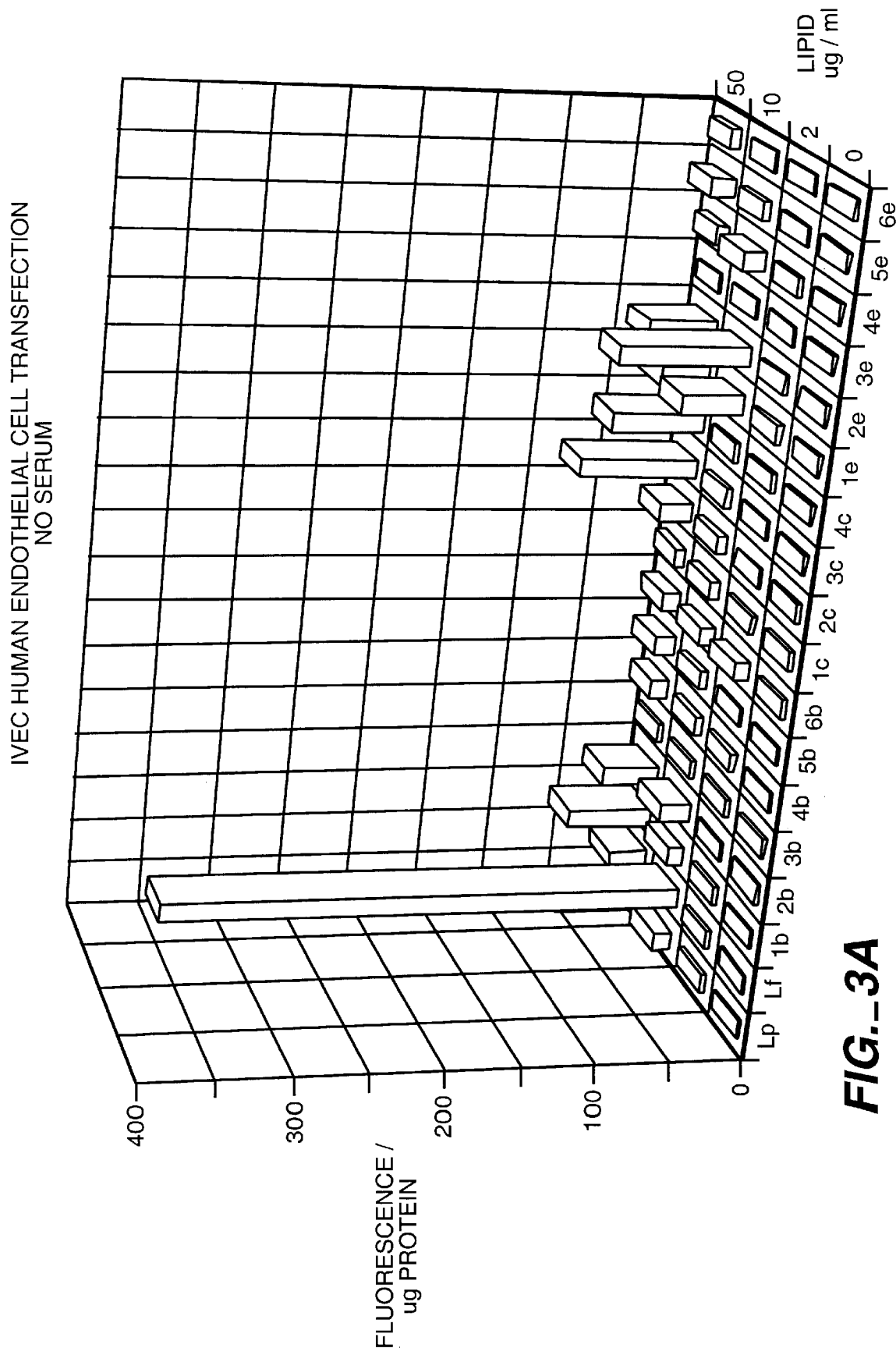

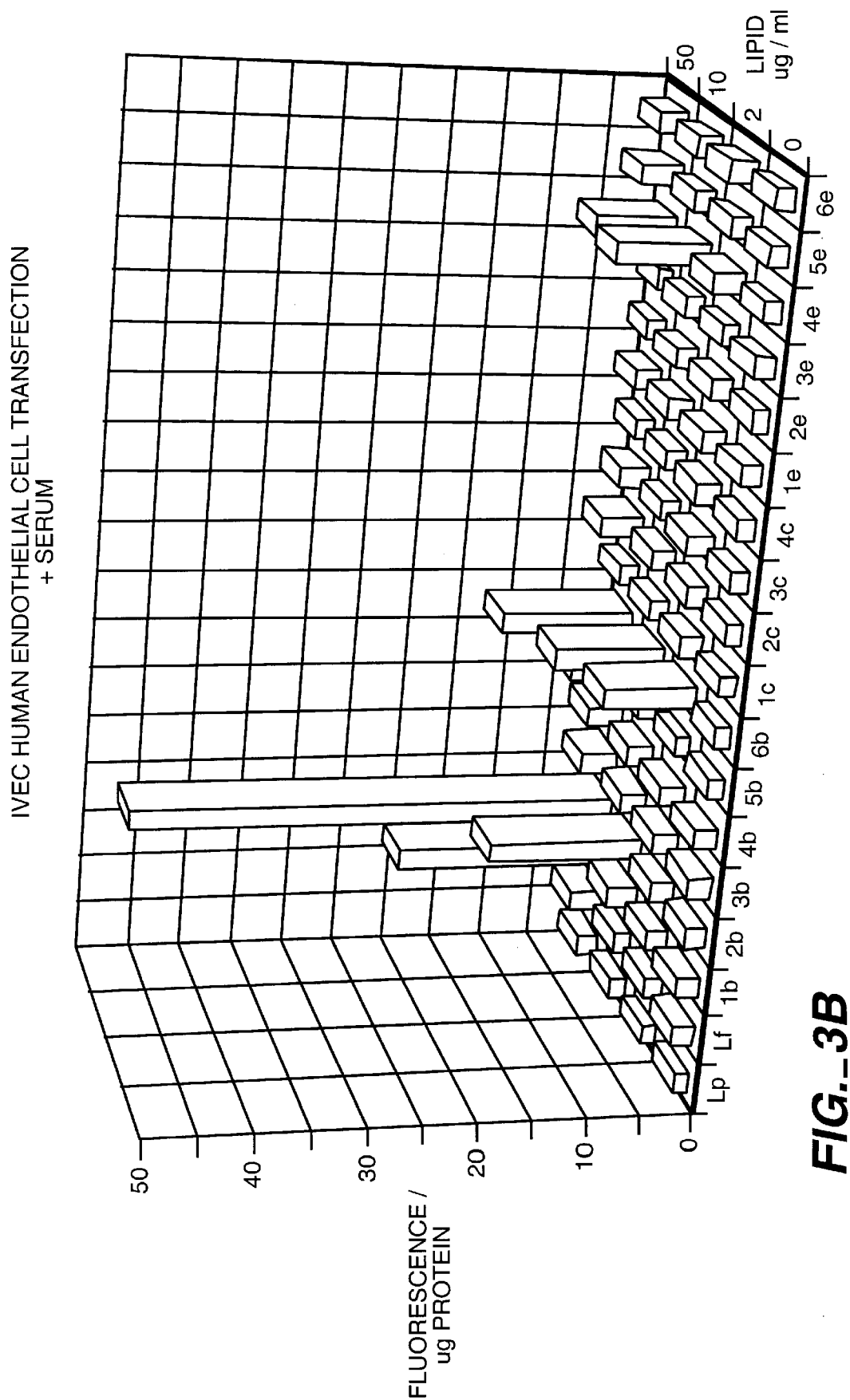
FIG._3B

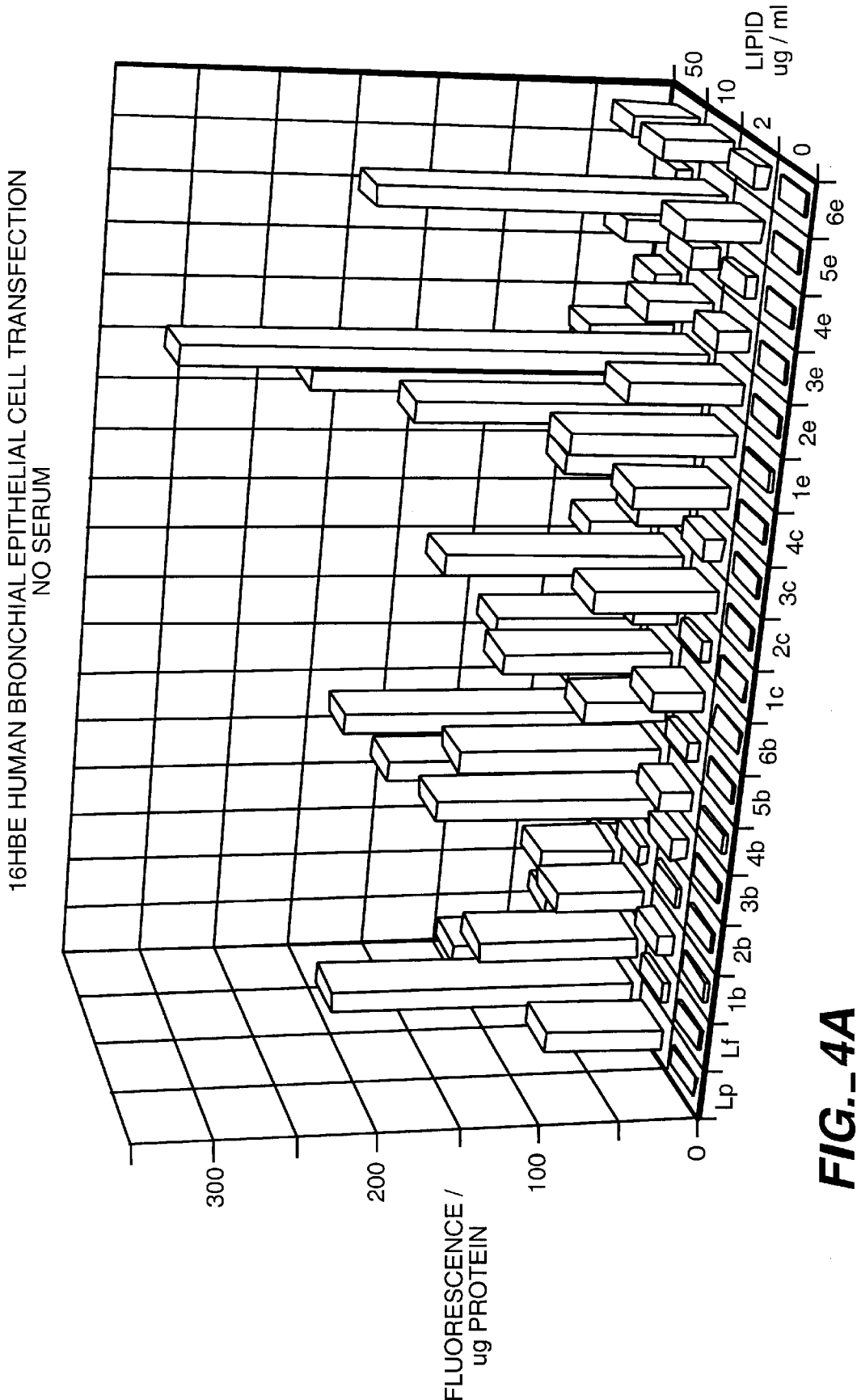
FIG._4A

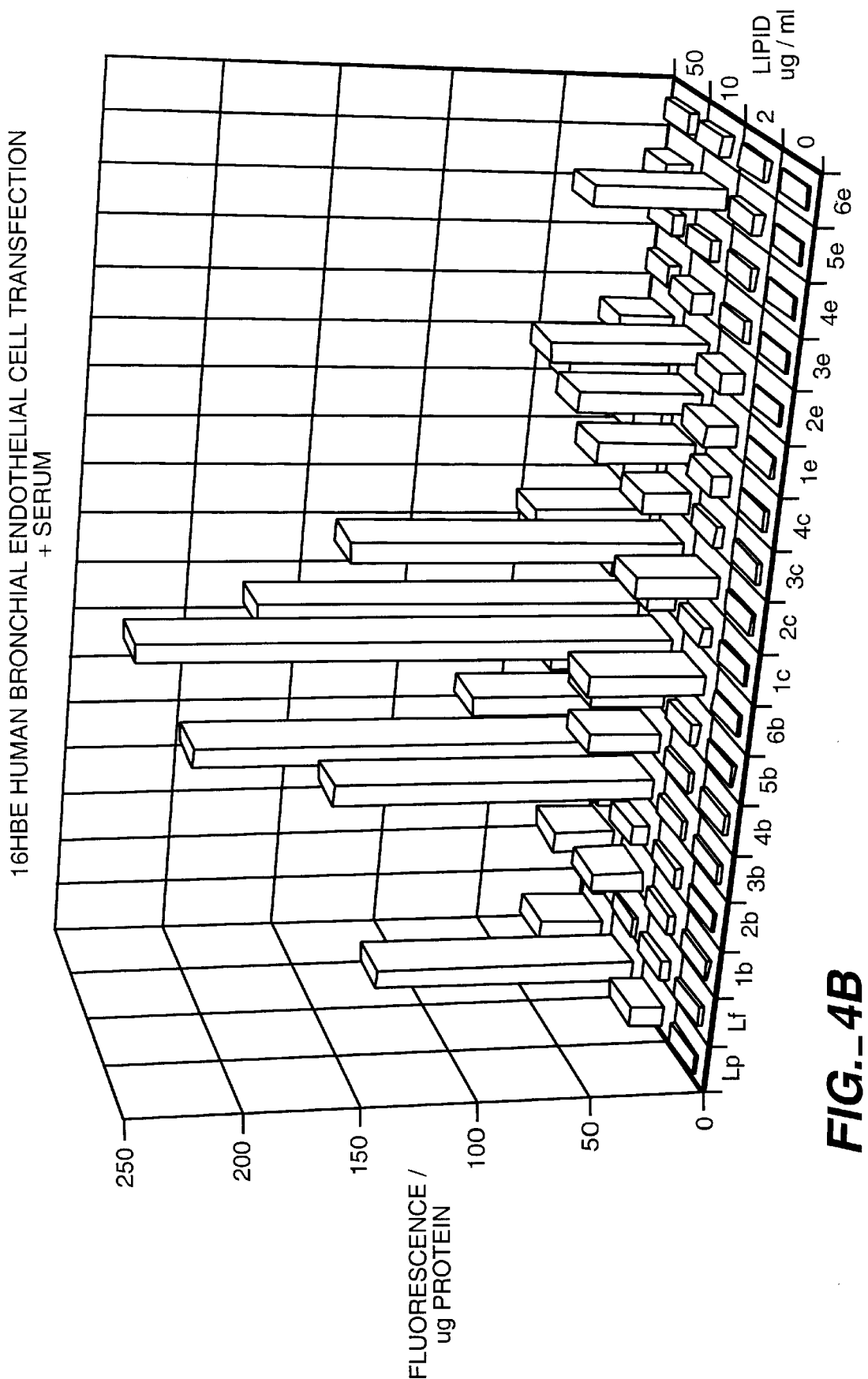
FIG._4B

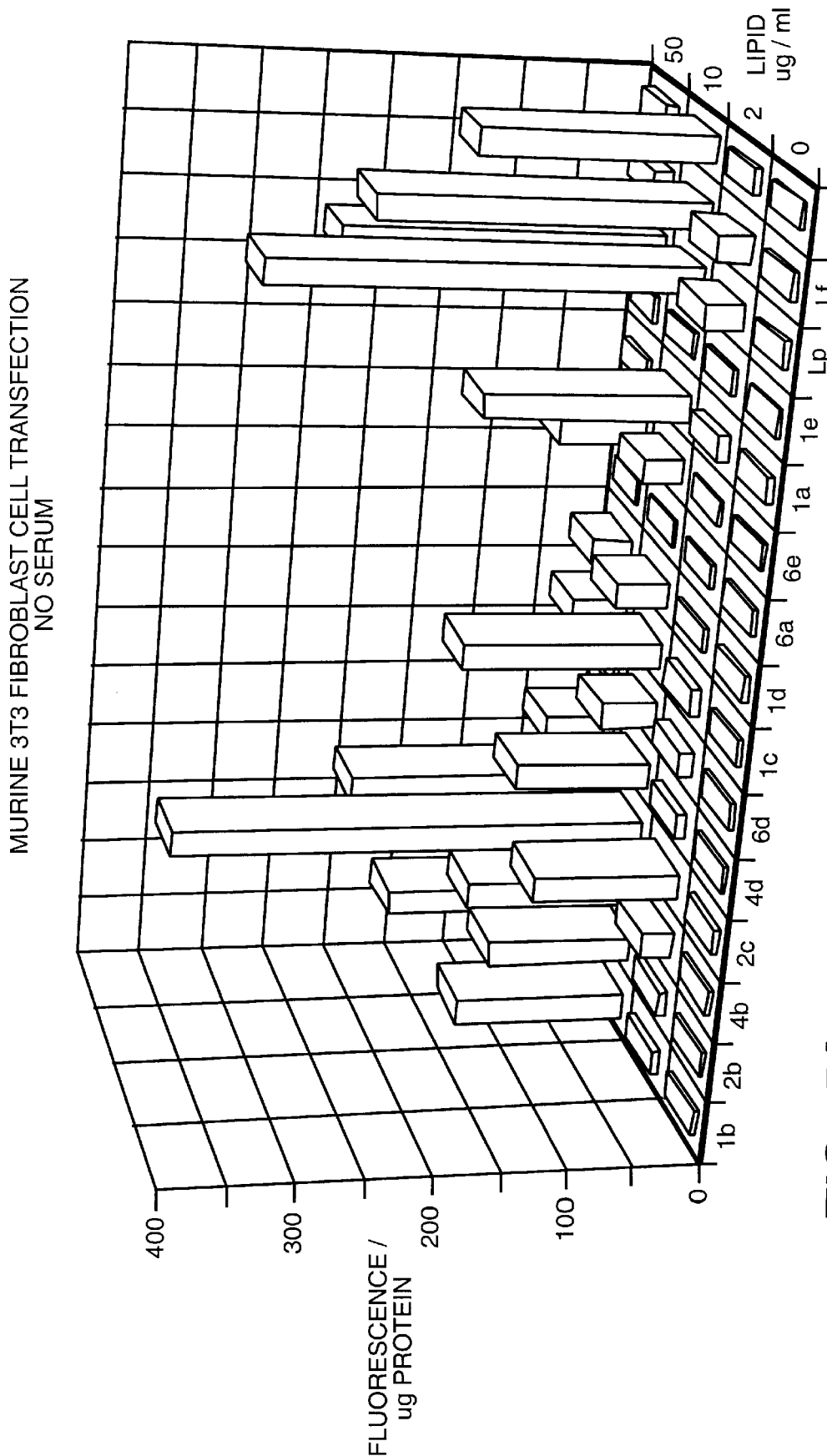
FIG._5A

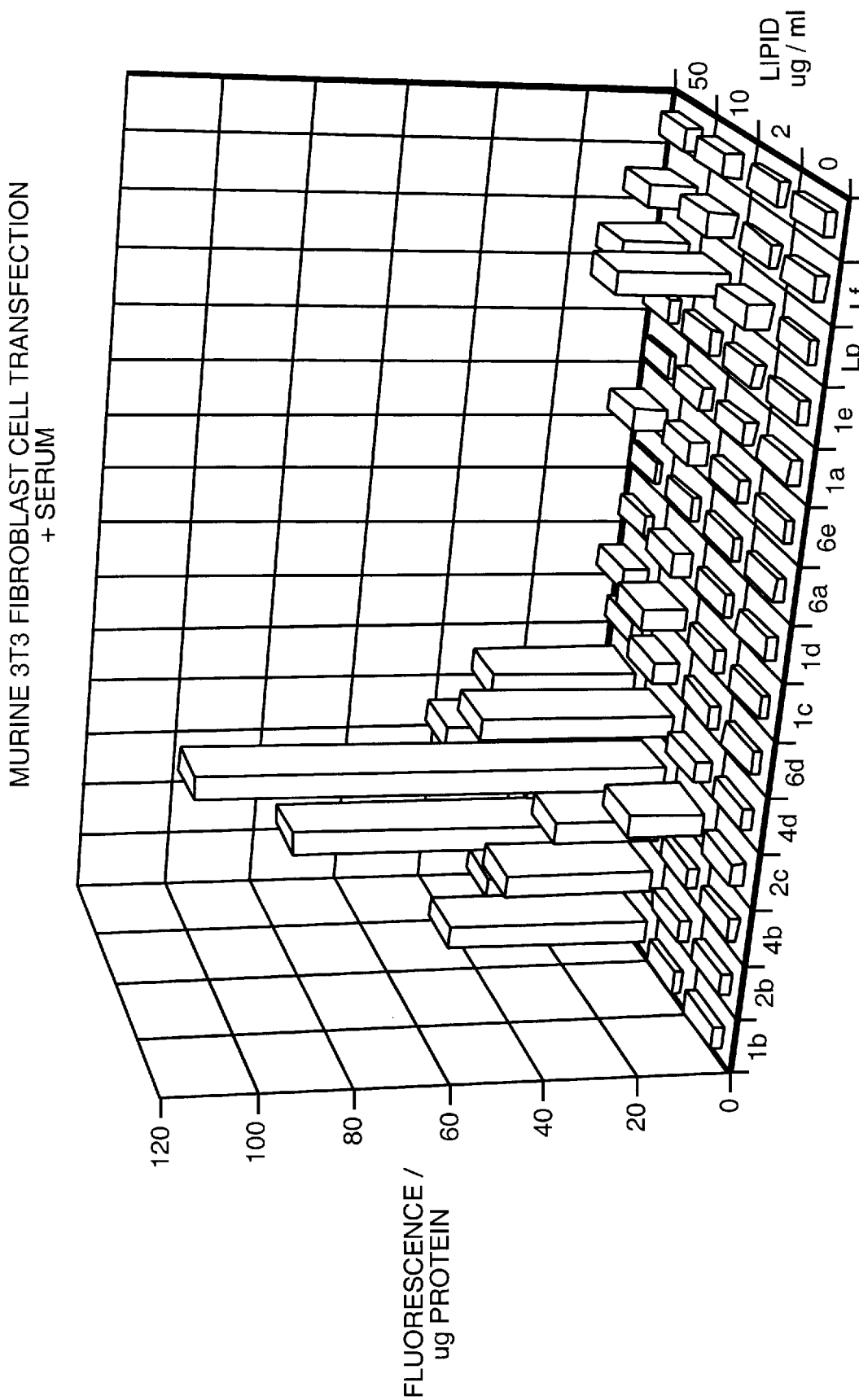
FIG._5B

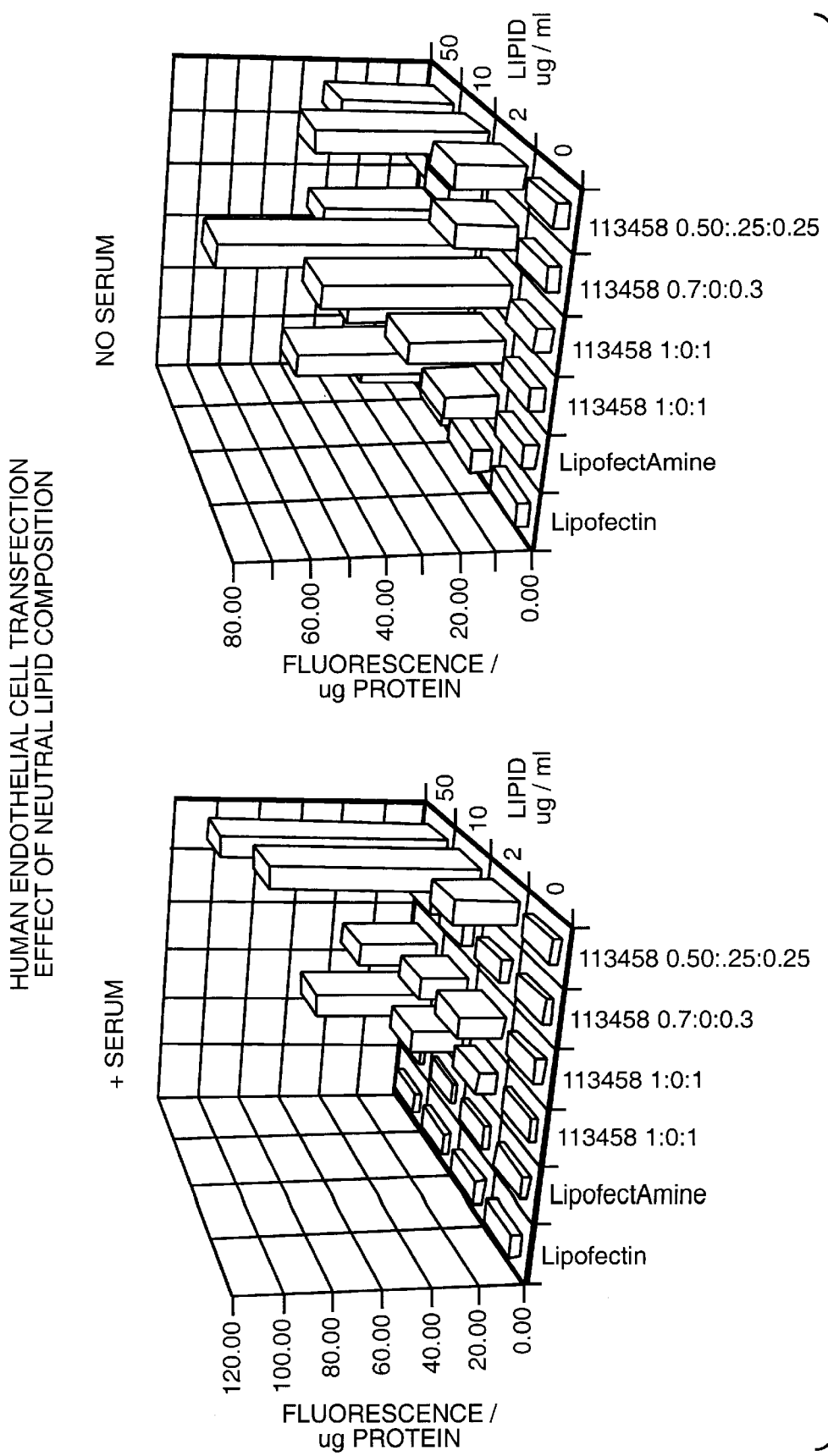
FIG._6

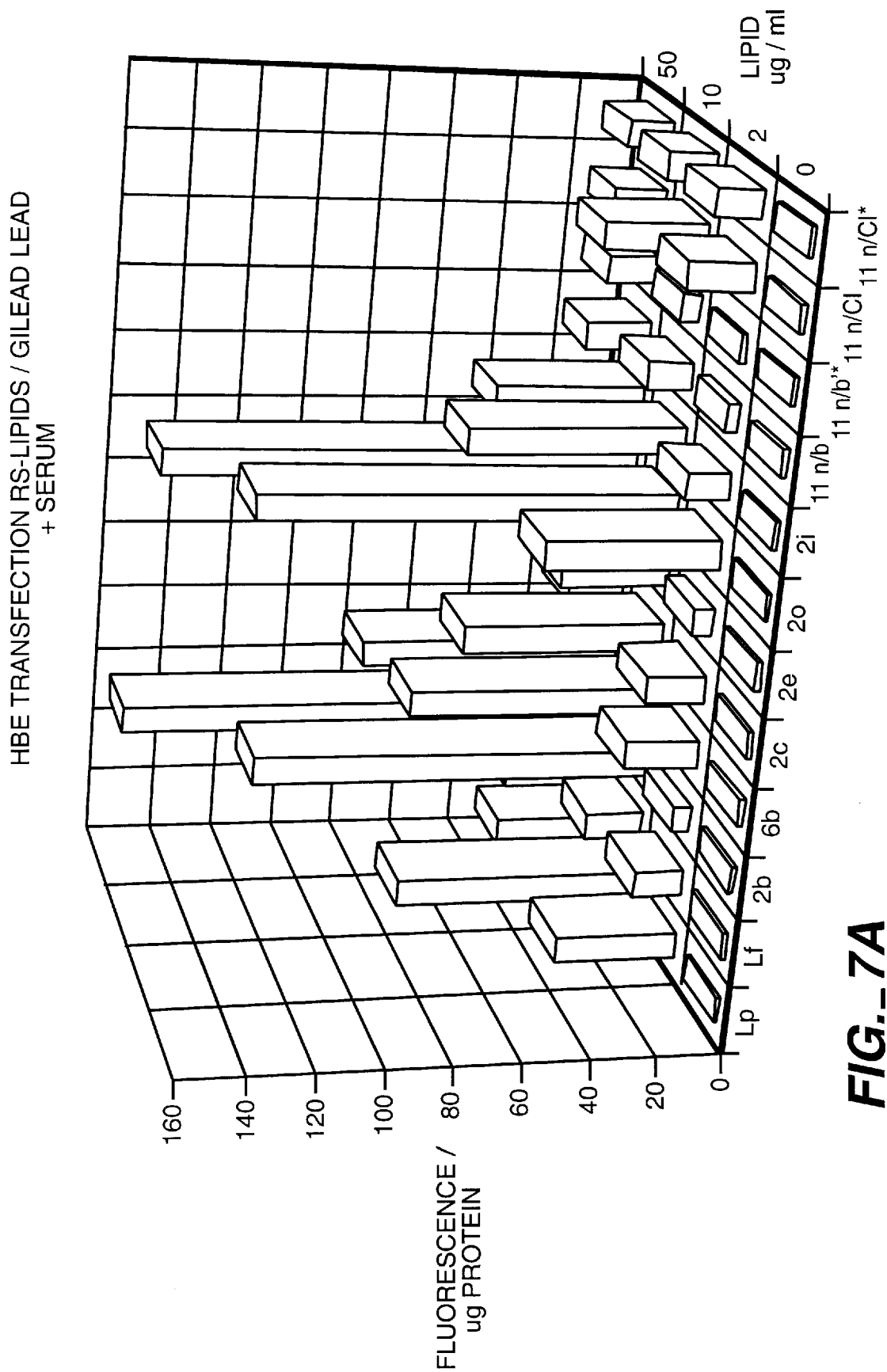
FIG._7A

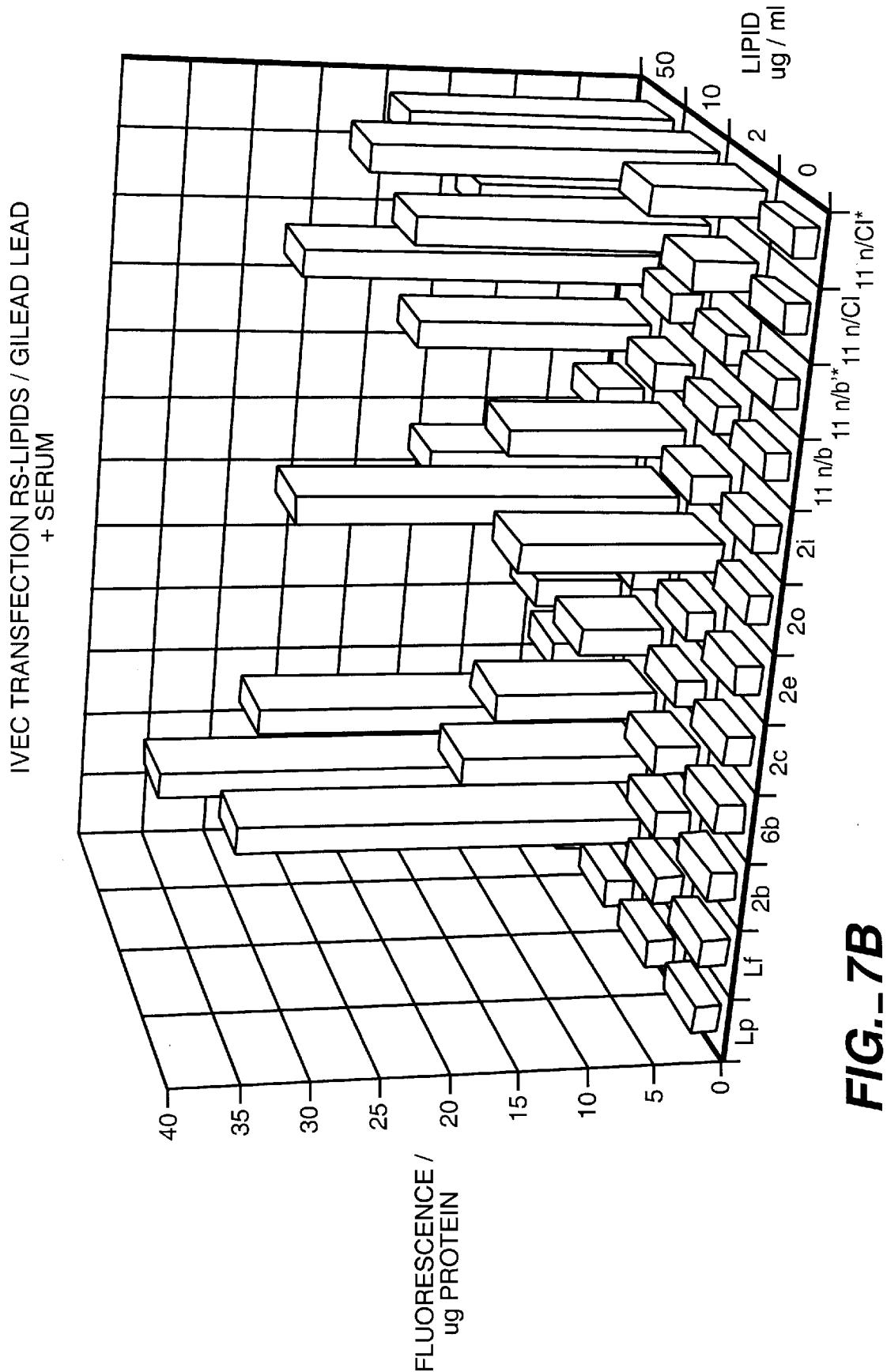
FIG._7B

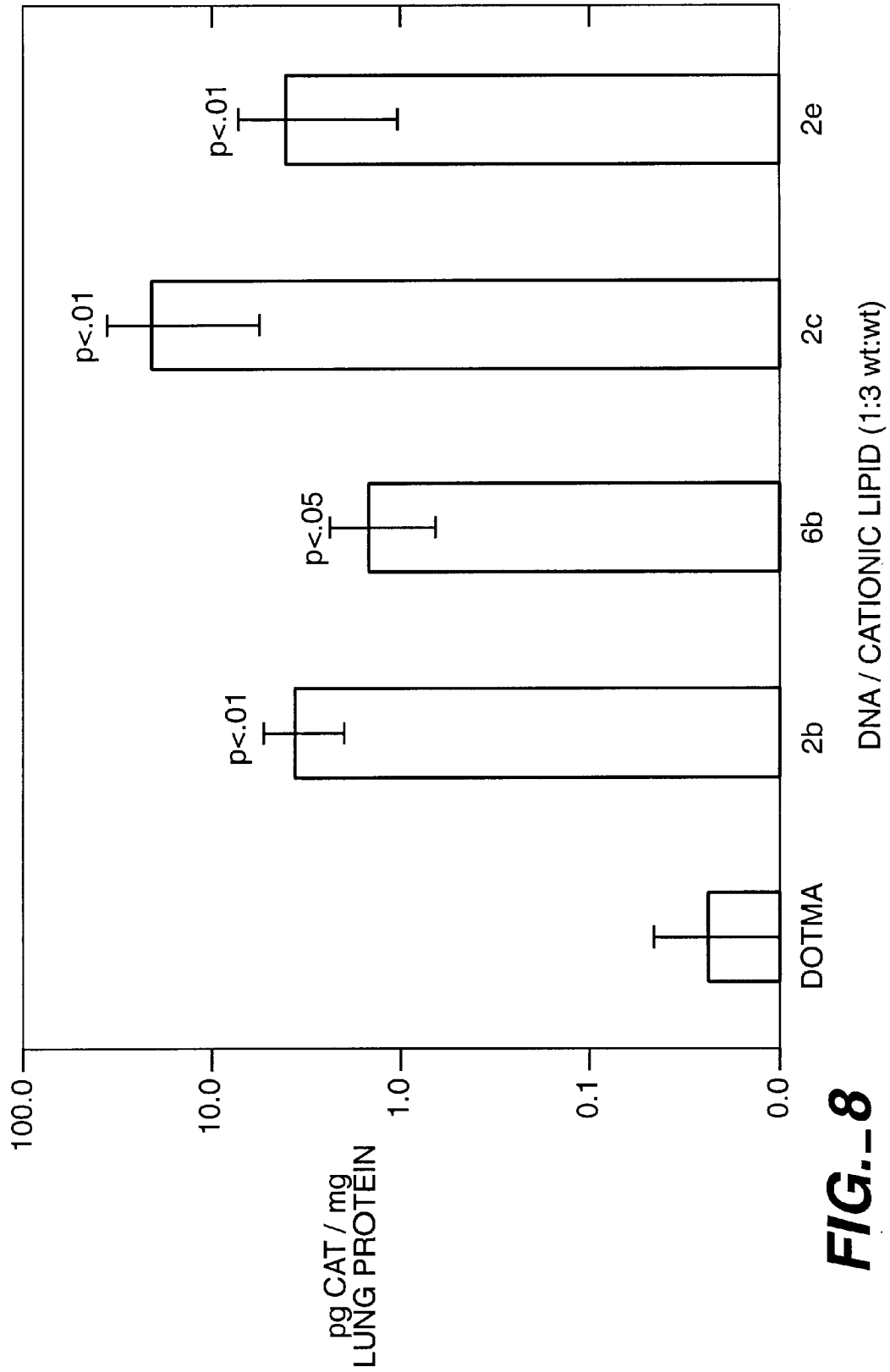

CATIONIC LIPIDS FOR GENE THERAPY

CROSS-REFERENCE TO RELATED APPLICATIONS

This application claims the benefit unde 35 U.S.C. 119(e) of U.S. Provisional Application Ser. No. 60/029,581, filed Oct. 22, 1996, and U.S. Provisional Application Ser. No. 60/049,922, filed Jun. 18, 1997.

BACKGROUND OF THE INVENTION

1. Field of the Invention

This invention relates to cationic lipid derivatives of guanidine, their preparation and use, and to pharmaceutical compositions using such derivatives.

2. Background Information

A number of lipid based materials, such as liposomes, have been used effectively as carriers in several pharmaceutical and biological situations to introduce biologically active substances such as drugs, radiotherapeutic agents, enzymes, viruses, nucleic acids,(e.g., plasmids, DNA and RNA constructs, transcription factors and other cellular vectors) into cultured cell lines and animals. For example, several lipid encapsulated drugs such as daunorubicin (DaunoXome™) and amphotericin B (Abelcet™, Ambisome™, Amphotec™) have recently been approved by the Food and Drug Administration(FDA) or are the subject of NDA filings under current FDA review.

In this vein, much effort has been directed towards developing lipid mediated methods for efficiently and efficaciously delivering genetic material directly to a biological cell. For example, gene therapy techniques alleviate disease states by transfecting target cells of a patient with nucleic acid constructs which are capable of affecting the processes of gene replication, transcription and translation in a therapeutically desirable manner. Typically, these nucleic acid constructs are high molecular weight, polyanionic molecules for which carrier-mediated delivery is usually required for successful transfection of cells either in vivo, ex vivo or in vitro. See, for example, U.S. Pat. No. 5,264,618, which describes a number of techniques for using lipid based carriers and such pharmaceutical compositions in clinical settings. Such transfection methods are also used in developing novel cell lines and animals which produce commercially significant proteins.

Several lipid carriers have recently been disclosed for plasmid delivery. See, U.S. Pat. Nos. 4,897,355; 4,946,787; 5,049,386; 5,366,737; 5,545,412 to Felgner et al., U.S. Pat. Nos. 5,264,618; 5,283,185 (to Epand et al. describing DC-chol); 5,334,761; PCT Publications WO 95/14381; WO 96/01840; WO 96/1841; and WO 96/18372 and Felgner et al., *Methods in Enzymology*, 5, 67–75 (1993). Although the compounds described in the above references facilitate the entry of biologically active substances into cells, it is still desirable to develop additional lipid carriers which provide higher uptake efficiencies, greater specificity and reduced toxicity. This invention fulfills this and related needs.

SUMMARY OF THE INVENTION

One aspect of the invention relates to a cationic lipid derivative of guanidine of Formula I:

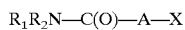

$$R_1R_2N—C(O)—A—X \qquad \text{Formula I}$$

wherein:

$R_1$ and $R_2$, which may be the same or different, are $C_{10}$–$C_{26}$ hydrocarbyl groups;

A is a hydrocarbylene group wherein one or more methylene groups is optionally replaced by a group Y (provided that none of the Y groups are adjacent to each other), where each Y is independently in the direction shown, —O—, —OC(O)—, —C(O)O—, —NR$_5$—, —NR$_5$C(O)—, —C(O)NR$_5$—, NR$_5$C(O)NR$_5$—, —NR$_5$C(O)O—, —OC(O)NR$_5$—, —S(O)$_n$— (where n is 0, 1 or 2) or —NZ—C(=NZ)NZ—, wherein each Z is independently H or —(CH$_2$)$_m$NR$_5$—C(=NR$_5$)NR$_5$ with m being an integer from 1–10, and each R$_5$ is independently H or lower alkyl;

X is: (1) a trihydrocarbylammonium group, wherein each hydrocarbyl group is the same or different to the others, or (2) —NH—C(=NR$_3$)NHR$_4$, wherein R$_3$ and R$_4$ are independently hydrocarbyl, haloalkyl, hydroxyalkyl, O-protected hydroxyalkyl, alkoxyalkyl, haloalkoxyalkyl, aryloxyalkyl, aminoalkyl, mono- or di-substituted aminoalkyl, N-protected-aminoalkyl, acyl, alkoxycarbonyl, aryloxycarbonyl, —C(O)NR$_6$R$_7$ (where R$_6$ and R$_7$ are independently H or hydrocarbyl), a nitrogen protecting group, or R$_3$ and R$_4$ together with the atoms to which they are attached form an optionally substituted monocyclic or bicyclic ring; provided that:

when $R_1$ and $R_2$ are both identical $C_{16}$ alkyl groups and X is —NH—C(=NH)NH$_2$, A is not a butylene chain; and salts, solvates, resolved and unresolved enantiomers, diastereomers and mixtures thereof.

Preferably, X is —NH—C(=NR$_3$)NHR$_4$. In other preferred aspects, $R_1$ and $R_2$ are identical and are monounsaturated alkenyl.

In other preferred aspects, $R_3$ and $R_4$ are identical and are H, a nitrogen protecting group, aminoalkyl or N-protected aminoalkyl.

In related aspects, the invention provides polyanion-lipid complexes comprising the cationic lipids of Formula I, methods for their preparation and their use in delivering biologically active substances to cells.

In another aspect, the invention relates to a pharmaceutical composition which comprises a therapeutically effective amount of a nucleic acid, a cationic lipid of Formula I, and an optional pharmaceutically acceptable excipient.

BRIEF DESCRIPTION OF THE DRAWINGS

FIG. 1 shows representative cationic lipid compounds of the invention represented as lipoamido tail groups having the depicted structures attached to head groups X.

FIG. 2 shows representative head groups X of the cationic lipid compounds of the invention.

FIGS. 3A and 3B demonstrate the comparative DNA transfection efficiency of human endothelial cells between commercially available compounds, Lipofectin™(Lp) and LipofectAmine™(Lf), and compounds of the present invention in serum-free (FIG. 3A) and serum-containing (FIG. 3B) medium.

FIGS. 4A and 4B demonstrate the comparative DNA transfection efficiency of human bronchial epithelial cells between commercially available compounds, Lipofectin™ (Lp) and LipofectAmine™(Lf), and compounds of the present invention in serum-free (FIG. 4A) and serum-containing (FIG. 4B) medium.

FIGS. 5A and 5B demonstrate the comparative DNA transfection efficiency of murine 3T3 fibroblast cells between commercially available compounds, Lipofectin™ (Lp) and LipofectAmine™(Lf), and compounds of the present invention in serum free (FIG. 5A) and serum-containing (FIG. 5B) medium.

FIG. 6 demonstrates the effect of co-lipids cholesterol and DOPE on the transfection efficiency of the novel compound 2-guanidino-N,N-di-octadec-9-enyl-propionamide (2B) in human endothelial cells in serum in serum-free (FIG. 6B) medium. The bracketed ratios are the ratios of 2B:cholesterol:DOPE in each experiment.

FIG. 7A demonstrates the transfection efficiency of compounds of the present invention relative other lipid compounds, Lipofectin™(Lp), LipofectAmine™(Lf) and GS-2888 (11n, used as the free base, 11n/b or the chloride salt, 11n/Cl) in epithelial cells.

FIG. 7B demonstrates the activity of several of the compounds tested in cultured vascular endothelial cells.

FIG. 8 shows the in vivo transfection efficiency of compounds of this invention relative to DOTMA™ when administered by airway installation into rats.

DETAILED DESCRIPTION

Definitions and General Parameters

A. Definitions

The following definitions are set forth to illustrate and define the meaning and scope of the various terms used to describe the invention herein.

The term "hydrocarbyl" refers to a monovalent hydrocarbon radical comprised of carbon chains or rings of up to 26 carbon atoms to which hydrogen atoms are attached. The term includes alkyl, cycloalkyl, alkenyl, alkynyl and aryl groups, groups which have a mixture of saturated and unsaturated bonds, carbocyclic rings and includes combinations of such groups. It may refer to straight chain, branched-chain, cyclic structures or combinations thereof.

The term "hydrocarbylene" refers to a divalent hydrocarbyl radical. Representative examples include alkylene, phenylene, cyclohexylene, dimethylenecyclohexyl, 2-butene-1,4-diyl, and the like. Preferably, the hydrocarbylene chain is fully saturated and/or has a chain of 1–10 carbon atoms.

The term "trihydrocarbylammonium" refers to the group $(R)_3N^+$— where each R is independently a hydrocarbyl radical, preferably lower alkyl.

An aliphatic chain comprises the classes of alkyl, alkenyl and alkynyl defined below. A straight aliphatic chain is limited to unbranched carbon chain radicals.

Alkyl refers to a fully saturated branched or unbranched carbon chain radical having the number of carbon atoms specified, or up to 26 carbon atoms if no specification is made. For example, alkyl of 1 to 8 carbon atoms refers to radicals such as methyl, ethyl, propyl, butyl, pentyl, hexyl, heptyl, and octyl, and those radicals which are positional isomers of these radicals. Lower alkyl refers to alkyl of 1 to 6 carbon atoms, such as methyl, ethyl, n-propyl, isopropyl, n-butyl, isobutyl, secbutyl, and tert-butyl. Alkyl of 6 to 26 carbon atoms includes hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl.

Alkenyl refers to any branched or unbranched unsaturated carbon chain radical having the number of carbon atoms specified, or up to 26 carbon atoms if no limitation on the number of carbon atoms is specified; and having 1 or more double bonds in the radical. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl and tetracosenyl, in their various isomeric forms, where the unsaturated bond(s) can be located anywhere in the radical and can have either the (Z) or the (E) configuration about the double bond(s).

Alkynyl refers to hydrocarbon radicals of the scope of alkenyl, but having 1 or more triple bonds in the radical.

The term "lower alkoxy" refers to the group —O—R' where R' is lower alkyl.

The term "polymethylene" refers to the group —(CH$_2$)$_n$— where n is an integer from 2 to 10.

The term "methylene" refers to the group —CH$_2$—.

The term "butylene" refers to the group —(CH$_2$)$_4$—

The term "alkylene" refers to a divalent saturated aliphatic radical.

The term "carbonyl" refers to the group —C(O)—.

The term "hydroxycarbonyl" or "carboxy" refers to the group —C(O)OH.

The term "lower-alkoxycarbonyl" refers to the group —C(O)OR' where R' is lower-alkyl.

The term "acyl" refers to the group —C(O)—R', where R' is hydrogen or hydrocarbyl, e.g., methylcarbonyl, ethylcarbonyl, benzoyl, naphthoyl and the like.

The term "carbamoyl" refers to the group —C(O)NR'R where R and R' are independently hydrogen or lower-alkyl, e.g., where R is hydrogen and R' is lower-alkyl the group is lower-alkylcarbamoyl, where R and R' are lower-alkyl the group is di-lower-alkylcarbamoyl.

The term "monosubstituted amino" refers to the group —NHR where R is hydrocarbyl or acyl.

The term "disubstituted amino" refers to the group NR'R" where R' and R" are independently hydrocarbyl or acyl.

The term "halo" refers to fluoro, bromo, chloro and iodo.

The term "aryl" refers to an aromatic monovalent mono- or poly-carbocyclic radical.

The term "(lower-alkyl)-hydroxylmethyl" refers to the group —CH(OH)—(lower-alkyl).

The term "arylmethyl" refers to the group aryl—CH$_2$—.

Aralkyl refers to an organic radical derived from alkyl radical in which a hydrogen atom is replaced by an aryl group. Representative examples are benzyl, phenethyl, 3-phenylpropyl, or the like.

Monocyclic rings generally have from 3 to 8 ring atoms.

Bicyclic rings generally have from 7 to 14 ring atoms.

Carbocyclic rings are those ring systems in which all ring atoms are carbon.

Heterocyclic rings (heterocycles, heterocyclo etc.) are those ring systems in which at least one ring atom is a heteroatom, typically O, N, or S(O)$_n$ (where n is 0, 1 or 2).

The term "protecting group" refers to a grouping of atoms which when attached to a reactive group in a molecule, masks, reduces or prevents that reactivity. Examples of protecting groups can be found in T. W. Greene et al., *Protective Groups in Organic Chemistry*, (Wiley, 2nd ed., 1991) and Harrison and Harrison et al., *Compendium of Synthetic Organic Methods*, Vols. 1–8, (John Wiley and Sons, 1971–1996). Representative amine protecting groups include the formyl group, or lower alkanoyl groups with 2 to 6 carbon atoms, in particular the acetyl or propionyl group, the trityl or substituted trityl groups, such as the monomethoxytrityl group,dimethoxytrityl groups such as the 4,4'-dimethoxytrityl or 4,4'-dimethoxytriphenylmethyl, the trifluoroacetyl group, allyloxycarbonyl, t-butyl carbamate (t-BOC), 1-adamantylcarbamate, benzyl carbamate (Cbz), 9-fluorenylmethyl carbamate (FMOC), nitroveratryloxycarbamate (NVOC), the phthalyl group and the like. Representative hydroxyl protecting groups are those where the hydroxyl is either acylated or alkylated and include benzyl and trityl ethers as well as alkyl ethers, tetrahydropyranyl ethers, trialkylsilyl ethers and allyl ethers Biologically active substance refers to any molecule or mixture or complex of molecules that exerts a biological effect in vitro and/or in vivo, including pharmaceuticals, drugs, proteins, vitamins, steroids, polyanions, nucleosides, nucleotides, polynucleotides, nucleic acids etc.

Buffers referred to in this disclosure include "Tris," "Hepes", and "PBS." "Tris" is tris(hydroxymethyl) aminomethane, and for the purposes of the preferred embodiments of this invention is used at about pH 7. "Hepes" is N-2-hydroxyethylpiperazine-N'-2-ethanesulfonic acid, also used here as a buffer at about pH 7. Phosphate-buffered saline, or "PBS," is 10 mM sodium phosphate and 0.9 wt. % NaCl, used as an isotonic physiological buffer at pH 7.4.

A polyanion is a biologically active polymeric structure such as a polypeptide, polynucleotide, nucleic acid, or other macromolecule wherein more than one unit of the polymer bears a negative charge and the net charge of the polymer is negative.

A complex (or a liposome complex) is defined as the product made by mixing pre-formed liposomes comprising a lipid of Formula I with a polyanion. Such a complex is characterized by an interaction between the polyanion and lipid components that results in the elution of the polyanion and liposome together as substantially one entity through a gel filtration column that separates on the basis of the Stokes' radius or by some other separation procedure.

A charge ratio refers to a quantitative relationship between the net positive charges contributed by the lipid and the net negative charges contributed by the polyanion in a complex. The charge ratio herein is expressed as positive to negative, i.e., 5:1 means five net positive charges on the lipid per net negative charge on the polyanion.

A liposome-polyanion complex is a composition of matter produced by contacting a solution of polyanion with a preparation of liposomes produced from a lipid of Formula I (with optional co-lipids as appropriate).

Optional or optionally means that the subsequently described event or circumstance may or may not occur, and that the description includes instances where said event or circumstance occurs and instances in which it does not. Optional substituents include, alkyl, cycloalkyl, alkenyl, alkynyl, aryl, haloalkyl, hydroxy, amino, halo, nitro, cyano, carboxy, carbamoyl, alkoxy, haloalkoxy, mono- and di-substituted amino, acyl, alkoxyacyl, aryloxyacyl and the like.

An optional co-lipid is to be understood as a structure capable of producing a stable liposome, alone, or in combination with other lipid components including the cationic guanidino lipids of this invention. It can be neutral, positively or negatively charged.

Double-coated complexes are prepared from liposome complexes bearing a net positive charge. Liposome complexes bearing a net positive charge are prepared using a greater molar amount of positively charged lipid than the molar amount of negative charge contributed by the polyanion. These positively charged complexes are mixed with negatively charged lipids to produce double-coated complexes. If sufficient negatively-charged lipid is added, the final complex has a net negative charge. This definition includes liposomes that have further modifications on the surface, such as the incorporation of antibodies or antigens therein.

DNA represents deoxyribonucleic acid, which may optionally comprise unnatural nucleotides. DNA may be single stranded, double stranded or in triple helix form.

RNA represents ribonucleic acid which may optionally comprise unnatural nucleotides. RNA may be single stranded or double stranded.

A polynucleotide is DNA or RNA containing more than one nucleotide. Polynucleotides can be made by chemical synthetic methodology known to one of ordinary skill in the art, or by the use of recombinant DNA technology, or by a combination of the two and include those incorporating unnatural nucleotides.

Antisense refers to a nucleotide sequence that is complementary to a specific sequence of nucleotides in DNA or RNA.

The term nucleic acid refers to DNA (e.g., genomic DNA, cDNA), RNA (e.g., mRNA, ribosomal RNA, tRNA, antisense RNA), ribozymes, oligonucleotides, polynucleotides, mixed duplexes and triplexes of DNA and RNA, plasmids, expression vectors etc., including those sequences containing unnatural nucleotides.

Drug refers to any therapeutic or prophylactic agent other than a food which is used in the prevention, diagnosis, alleviation, treatment, or cure of disease in man or animal. (Therapeutically useful polynucleotides, nucleic acids and polypeptides are within the scope of this definition for drugs).

A pharmaceutical formulation is a composition of matter including a drug, for therapeutic administration to a human or animal.

A pharmaceutically acceptable anion is an anion which itself is non-toxic or otherwise pharmaceutically acceptable and which does not render the compound pharmaceutically unacceptable. Examples of such anions are the halide anions, chloride, bromide, and iodide. Inorganic anions such as sulfate, phosphate, and nitrate may also be used. Organic anions may be derived from simple organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, trifluoroacetic acid and the like.

A stable transfectant is a living cell into which DNA has been introduced and become integrated in the genomic DNA of that cell.

Topical administration includes application to any surface of the body, including ocular administration and administration to the surface of any body cavities.

Transdermal administration is administration through the skin with a systemic effect.

Transfection refers for the purposes of this disclosure to the introduction of DNA or RNA into a living cell Unnatural nucleotides include those which are commercially available or which can be readily made by means known to those of ordinary skill in the art.

The term "pharmaceutically acceptable salt" refers to any salt derived from an inorganic or organic acid or base.

As used herein, the terms "treatment" or "treating" of a condition and/or a disease in a mammal, means:

(i) preventing the condition or disease, that is, avoiding any clinical symptoms of the disease;

(ii) inhibiting the condition or disease, that is, arresting or reducing the development or progression of clinical symptoms; and/or (iii) relieving the condition or disease, that is, causing the regression of clinical symptoms.

As used herein, the term "therapeutically effective amount" refers to that amount of a biologically active substance which, when administered to a mammal in need thereof, is sufficient to effect treatment. The amount that constitutes a "therapeutically effective amount" will vary depending on the substance, the condition or disease and its severity, and the mammal to be treated, but may be determined routinely by one of ordinary skill in the art with regard to contemporary knowledge and to this disclosure.

All temperatures are given in degrees Celsius (i.e., °C.).

Unless specified to the contrary, the reactions described herein take place at atmospheric pressure over a temperature range from about −78° C. to about 150° C., more preferably from about 10° C. to about 50° C., and most preferably at about room (or "ambient") temperature, e.g., about 20° C. Unless specified to the contrary, the ranges of time and temperature described herein are approximate, e.g., "from 8 to 24 hours at from 10° C. to 100° C." means from about 8 to about 24 hours at about 10° C. to about 100° C.

Isolation and purification of the compounds and intermediates described herein can be effected, if desired, by any suitable separation or purification procedure such as, for example, filtration, extraction, crystallization, column chromatography, preparative high pressure liquid chromatography (preparative HPLC), thin-layer chromatography or thick-layer chromatography, or a combination of these procedures. Specific illustrations of suitable separation and isolation procedures can be had by reference to the examples hereinbelow. However, other equivalent separation or isolation procedures can also be used.

Some representative compounds are named in the following examples.

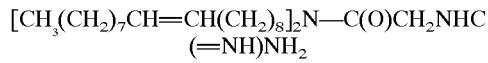

2-Guanidino-N,N-di-octadec-9-enyl-acetamide

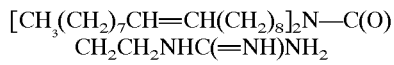

3-Guanidino-N,N-di-octadec-9-enyl-propionamide

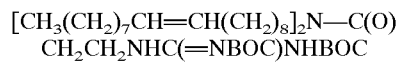

3-[N',N"-bis(tertbutyloxycarbonyl)guanidino]-N,N-di-octadec-9-enyl-propionamide

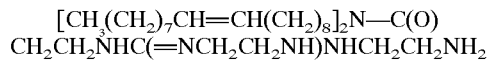

3-[N',N"-bis(2-aminoethyl)guanidino]-N,N-di-octadec-9-enyl-propionamide

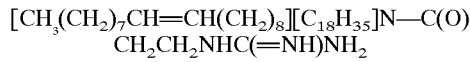

3-Guanidino-N-octadec-9-enyl-N-octadecyl-propionamide

Compounds are also represented and identified with reference to the structures shown in FIGS. 1 and 2. In this representation, the compounds are represented as a lipoamido tail group attached to a cationic head group X. FIG. 1 shows representative lipoamido tail groups 1–14, and FIG. 2 shows structures of representative cationic head groups A–U. Therefore, a compound defined as 1B refers to the compound in which the lipoamido tail group 1 is attached to cationic head group B, i.e., 2-guanidino-N,N-di-octadec-9-enyl-acetamide.

Compounds of the Invention

Compounds of this invention are novel cationic lipid derivatives of Formula I:

$$R_1R_2N—C(O)—A—X \quad \text{Formula I}$$

wherein:

$R_1$ and $R_2$, which may be the same or different, are $C_{10}$–$C_{26}$ hydrocarbyl groups;

A is a hydrocarbylene group wherein one or more methylene groups is optionally replaced by a group Y (provided that none of the Y groups are adjacent to each other), where each Y is independently in the direction shown, —O—, —OC(O)—, —C(O)O—, —NR$_5$—, —NR$_5$C(O)—, —C(O)NR$_5$—, NR$_5$C(O)NR$_5$—, —NR$_5$C(O)O—, —OC(O)NR$_5$—, —S(O)$_n$— (where n is 0, 1 or 2) or —NZ—C(=NZ)NZ—, wherein each Z is independently H or —(CH$_2$)$_m$NR$_5$—C(=NR$_5$)NR$_5$ with m being an integer from 1–10, and each R$_5$ is independently H or lower alkyl;

X is: (1) a trihydrocarbylammonium group, wherein each hydrocarbyl group is the same or different to the others, or (2) —NH—C(=NR$_3$)NHR$_4$, wherein R$_3$ and R$_4$ are independently hydrocarbyl, haloalkyl, hydroxyalkyl, O-protected hydroxyalkyl, alkoxyalkyl, haloalkoxyalkyl, aryloxyalkyl, aminoalkyl, mono- or di-substituted aminoalkyl, N-protected-aminoalkyl, acyl, alkoxycarbonyl, aryloxycarbonyl, —C(O)NR$_6$R$_7$ (where R$_6$ and R$_7$ are independently H or hydrocarbyl), a nitrogen protecting group, or R$_3$ and R$_4$ together with the atoms to which they are attached form an optionally substituted monocyclic or bicyclic ring;

provided that:

when $R_1$ and $R_2$ are both identical $C_{16}$ alkyl groups and X is —NH—C(=NH)NH$_2$, A is not a butylene chain;

and salts, solvates, resolved and unresolved enantiomers, diastereomers and mixtures thereof.

Preferably, X is —NH—C(=NR$_3$)NHR$_4$. In other preferred aspects, $R_1$ and $R_2$ are identical and are monounsaturated alkenyl.

In other preferred aspects, $R_3$ and $R_4$ are identical and are H, a nitrogen protecting group, aminoalkyl, N-protected aminoalkyl, hydroxyalkyl or O-protected hydroxyalkyl. Frequently $R_3$ and $R_4$ are aminoalkyl groups represented by —(CH$_2$)$_p$—NH$_2$ where p is an integer from 2 to 10. The amino group may also be protected, preferably by a tert-butyloxycarbonyl group. It will also be recognized that alkylamino groups may be quarternized or present as the corresponding N-oxides.

Synthesis of the Compounds of Formula I

As used in the Reaction Schemes, $R_1$, $R_2$, $R_3$, $R_4$, $R_5$, $R_6$ and $R_7$ are the same as described in the Summary of the Invention.

Reaction Scheme A illustrates a representative scheme for the preparation of novel cationic lipid derivatives of guanidine, i.e., compounds of Formula I.

Reaction Scheme B illustrates a representative scheme for preparing the unsymmetrical amines $R_1R_2$NH used as starting materials in Reaction Scheme A.

Reaction Scheme A

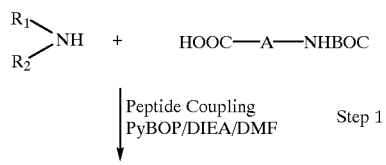

-continued

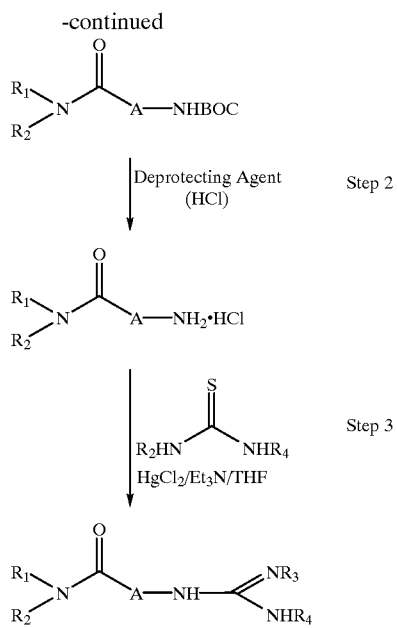

Reaction Scheme B

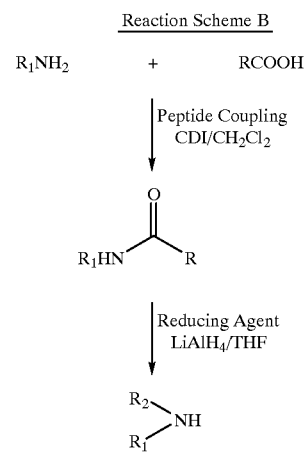

Starting Materials

Referring to Reaction Schemes A and B, the starting materials are available from Aldrich Chemicals Co., Inc., Fluka Chemical Corporation, K&K Chemicals, Eastman Kodak Chemicals, Lancaster Synthesis Ltd., Karl Industries, Maybridge Chemical Co. Ltd., or Tokyo Kasai International. Long chain acids are preferably obtained from Nu Chek Prep Inc., (Elysian, Minn.). Those compounds that are not commercially available can be prepared by one of ordinary skill in art following procedures set forth in references such as, "Fieser and Fieser's Reagents for Organic Synthesis", Volumes 1–15, John Wiley and Sons, 1991; "Rodd's Chemistry of Carbon Compounds", Volumes 1–5 and Supplementals, Elsevier Science Publishers, 1989; and "Organic Reactions", Volumes 1–40, John Wiley and Sons, 1991.

Preparation of Amines $R_1R_2NH$

With reference to Reaction Scheme B, intermediates of structure $R_1R_2NH$ can be synthesized by first coupling an amine of formula $RNH_2$ with a carboxylic acid of formula $R_1COOH$ in the presence of an activating group such as N-hydroxy succinimide, p-nitrophenol, pentachlorophenol, pentafluorophenol and the like and a coupling reagent such as dicyclohexylcarbodiimide (DCC), diisopropylcarbodiimide (DIC), N-hydroxybenzotriazole (HBOT), N-hydroxybenzotriazolephosphoryl chloridate, isobutyl chloroformate, N,N'-carbonyldiimidazole or the like. The coupling is generally done in an anhydrous, nonhydroxylic organic solvent. The resulting amide is then reduced with a reducing agent such as a metal hydride (e.g., lithium aluminum hydride, diborane or the like) to give the desired amine $R_1R_2NH$.

Amines $RNH_2$ and acids $R_1COOH$ are generally commercially available. Amines $RNH_2$ may also be prepared by reduction of a precursor carboxamide (available in turn from the corresponding acid via the acid chloride) . Acids $R_1COOH$ may be purchased or are available by oxidation of the precursor alcohols which are also frequently available.

Preparation of Compounds of Formula I

Bifunctional linkers $HOC(O)$—A—$NH_2$ (A being as defined earlier) carrying an amine on one end and a carboxylic acid at the other end are either commercially available from suppliers such as Sigma Chemical Company (St. Louis, Mo.) or may be prepared using standard methods known to one of skill in the art. With reference to Reaction Scheme A, the amine is protected and the carboxyl group of the resulting N-protected linker is then coupled to an amine of formula $R_1R_2NH$ in step 1 under conditions similar to those described above. In step 2, the nitrogen protecting group is removed under appropriate conditions, (acid treatment, hydrogenolysis, photolysis etc.) and the resulting free amine is condensed in step 3 with a thiourea or an isothiouronium salt to give a compound of Formula I. Thioureas and isothiouronium salts are either commercially available or can be prepared using the synthetic procedures described in Org. Syn. Coll., Vol. II (S-methyl isothiourea sulfate), Org. Syn. Coll., Vol. III (S-ethylthiourea) and Chem. Reviews, 55, 181 (1955). Compounds of Formula I in which X is trihydrocarbylammmonium can be obtained by alkylating the free amine obtained in step 2 with the requisite alkylating agents, e.g., a trihydrocarbyl iodide, p-toluenesulfonate, mesylate and the like, sequentially if necessary.

The compounds of this invention may be conveniently represented as a lipoamido tail group attached to a cationic head group X. Representative lipoamido tail groups are shown in FIG. 1 where X represents the cationic head group Representative cationic head groups X are shown in FIG. 2. Frequently, the cationic head group is a guanidino moiety. Using the representation of FIGS. 1 and 2, Table 1 shows a representative sampling of the compounds of this invention prepared using the methods described above and in the Examples.

| Lipoamido tail group | Cationic head group |
|---|---|
| 1 | A, B, C, D, E |
| 2 | A, B, C, D, E, F, G, H, I, J, M, O, P, Q, R, S, T, U |
| 3 | A, B, C, D, E |

-continued

| Lipoamido tail group | Cationic head group |
|---|---|
| 4 | A, B, C, D, E |
| 5 | A, B, D, E |
| 6 | A, B, D, E |
| 7 | A, B |
| 8 | A, B, R |
| 9 | B |
| 10 | B |
| 11 | B, N |
| 12 | B, M, N |
| 13 | B |
| 14 | B |

Preferred Compounds

Presently preferred are the compounds of Formula I where $R_1$ and $R_2$ are $CH_3(CH_2)_7CH=CH(CH_2)_8-$.

Especially preferred is the compound of Formula I where $R_3$ and $R_4$ are alkylamino (optionally N-protected) or tert-butyloxycarbonyl, and $R_1$ and $R_2$ are $CH_3(CH_2)_7CH=CH(CH_2)_8-$.

Utility

The cationic lipids of this invention are typically used as carriers for various biologically active substances, such as drugs or nucleic acids. In particular, the cationic lipids can be used alone or combined with other lipids in formulations for the preparation of lipid complexes for the intracellular delivery of such biologically active substances. Uses contemplated for the cationic guanidino lipids of this invention include transfection procedures corresponding to those presently practiced with commercial cationic lipid preparations, such as Lipofectin™, and other published techniques using conventional cationic lipid delivery technology. The cationic lipids of this invention can be used in pharmaceutical formulations to deliver therapeutic agents by various routes, in vivo or ex vivo, and to various sites of a mammal to achieve a desired therapeutic effect. They may also be used in vitro to transfect and prepare cell lines which express proteins of commercial significance.

Preparation of Lipid Complexes

Liposomes containing the cationic lipids of this invention are prepared by methods known to those of skill in the art. Generally, a solution of the cationic lipid (with one or more optional co-lipids) in an organic solvent is dried to provide a lipid film which is then rehydrated to provide a suspension of liposomes. A suitable solvent for preparing a dried lipid film from the desired lipid components is to be understood as any solvent that can dissolve all of the components and then be conveniently removed by evaporation or lyophilization. Exemplary solvents are chloroform, dichloromethane, diethylether, cyclohexane, cyclopentane, benzene, toluene, methanol, or other aliphatic alcohols such as propanol, isopropanol, butanol, tert-butanol, isobutanol, pentanol and hexanol. Mixtures of two or more solvents may be used in the practice of the invention.

A suitable aqueous medium for forming liposomes from the dried lipid film is to be understood as, for example, water, an aqueous buffer solution, or a tissue culture media. For example, a suitable buffer is phosphate buffered saline, i.e., 10 mM potassium phosphate having a pH of 7.4 in 0.9% NaCl solution. The pH of the medium should be in the range of from about 2 to about 12, but preferably about 5 to about 9, and most preferably about 7. In some situations, the biologically active substances will be included in the rehydration medium, whereas in other cases, as with nucleic acids, they will be added subsequent to the rehydration/formation of the liposomes.

Examples of optional co-lipids are phospholipid-related materials, such as lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoylphosphatidylethanolamine (POPE) and dioleoylphosphatidylethanolamine 4-(N-maleimidomethyl)cyclohexane-l-carboxylate (DOPE-mal). Additional non-phosphorous containing lipids are, e.g., stearylamine, dodecylamine, hexadecylamine, acetyl palmitate, glycerol ricinoleate, hexadecyl stearate, isopropyl myristate, amphoteric acrylic polymers, triethanolamine-lauryl sulfate, alkyl-aryl sulfate polyethyloxylated fatty acid amides, dioctadecyldimethyl ammonium bromide and steroids such as cholesterol, ergosterol, ergosterol B1, B2 and B3, androsterone, cholic acid, desoxycholic acid, chenodesoxycholic acid, lithocholic acid and the like. Preferred colipids are cholesterol and/or DOPE.

Optionally, the suspension may be subjected to a sonication, reverse phase evaporation, freeze-thaw or extrusion process to produce liposomes of a specified size range. Preferably, unilamellar liposomes of about 50 to about 200 $\mu$M in diameter are prepared. The biologically active substance being delivered is then mixed with the liposomal suspension to produce a lipid complex of the biological substance.

The net charge on the complex is determined by the charge on the liposomes, the charge on the biological substance and the relative amounts of each being used. Thereby, either cationic or anionic lipid complexes may be prepared. It is generally preferable to avoid neutrality when the complexes are being prepared, especially when they are being prepared for in vivo delivery of a nucleic acid. Typically this is accomplished by adding the minor component (on a charge basis) to the major component with vigorous stirring to avoid local concentration gradients. Thus, when an anionic complex is being prepared, the cationic liposome suspension is added to the nucleic acid, whereas when a cationic complex is being prepared the order of addition is reversed. It has been generally observed that anionic complexes are more suitable for airway delivery of nucleic acids, whereas intravenous delivery is more effectively accomplished with cationic complexes.

Pharmaceutical Formulations

The present invention provides pharmaceutical compositions comprising a cationic lipid as described above and one or more biologically active substances. Such pharmaceutical compositions facilitate intracellular entry of biologically active molecules into tissues and organs such as the airway epithelium, the lung, heart, gastric mucosa and solid tumors. Additionally these compositions facilitate entry of the biologically active substances into cells maintained in vitro.

Biologically Active Substances

Biologically active substances included in the pharmaceutical formulations of this invention include drugs and nucleic acids. As described herein, nucleic acids include genomic DNA, cDNA, RNA, mRNA, ribosomal RNA, antisense RNA, ribozymes, mixed duplexes and triplexes of RNA and DNA and plasmids. Nucleic acids also include those species in which the naturally occurring bases, carbohydrate residues and/or phosphodiester linkages have been modified as well as peptide nucleic acids. Such modifications include phosphorothioates, substitution of non-natural bases and the like, including but not limited to those species disclosed in PCT Publications WO 96/1840 and WO 96/1841.

Frequently, nucleic acids will code for therapeutically or diagnostically significant proteins. Such proteins include histocompatibility antigens, cell adhesion molecules, growth factors(e.g., vascular endothelial growth factor for peripheral arterial disease), recombinant human Factor VIII, hormones (insulin, growth hormone, growth hormone releasing factor), cytokines (e.g. IL-12), chemokines, antibodies, antibody fragments, cell receptors, intracellular enzymes, transcription factors (e.g., NF-κB, IκB), toxic peptides (such as ricin A chain, diphtheria toxin etc., which are capable of eliminating diseased or malignant cells) or any fragment or modification of any of these. It will be understood that such proteins include truncates and muteins of wild type proteins and may act as agonists or antagonists of the wild type variant depending on the therapeutic need.

The nucleic acids may also comprise expression control sequences and will generally have a transcriptional unit comprising a transcriptional promoter, an enhancer, a transcriptional terminator, an operator or other control sequences. It will frequently be desirable to have a tissue-specific promoter which will ensure that the protein is expressed specifically in the target tissue. Nucleic acids encoding diagnostically significant proteins will often carry additional sequences encoding for selectable or diagnostic markers (e.g., lacZ, β-galactosidase, chloramphenicol transferase, etc.).

The cationic lipid-nucleic acid formulations of this invention may also contain ligands and/or receptors capable of binding to a component of the cell. A ligand is any compound of interest which can specifically bind to another molecule, referred to as a receptor, the ligand and the receptor forming a complementary pair. For example, a ligand may be an antibody against a cell surface receptor, such as the antigens of the major histocompatibility complex, HLA-A. Such formulations allow one to specifically target the nucleic acids to a particular subset of cells which express the receptor on their surface. Alternatively, a ligand may be a small molecule, such as an inhibitor of an intracellular enzyme, such as angiotensin converting enzyme. Ligands may be covalently linked to the cationic lipid or noncovalently embedded in the liposomal membrane.

Transfection

Cationic lipid-nucleic acid complexes of the present invention were used to transfect cells both in vitro and in vivo. In vitro experiments were performed both in the presence and absence of serum. Transfection efficiencies were determined relative to commercial cationic lipid formulations, such as Lipofectin™, DOTMA™, as well as more recently disclosed cationic lipids such as Cytofectin GS-2888 (J. G. Lewis et al., Proc. Nat. Acad. Sci. (USA), Vol. 93, 3176–3181 (1996). Transfection efficiencies were determined using the PCMVβ plasmid carrying a lacZ/β-galactosidase detectable marker. As shown in more detail in the Examples section, the transfection efficiency of the subject cationic lipids in the presence of serum was consistently higher compared to either Lipofectin™ or GS-2888. Though not wishing to be bound by any particular theory, it is believed that this surprising superiority afforded by the cationic guanidino lipids disclosed herein is due to the guanidino head groups binding more tightly to DNA and thus being less available for binding to serum proteins.

Cell types which may be transfected using lipid mediated delivery using cationic lipids of this invention include, but are not limited to endothelial cells, epithelial cells (particularlyl lung epithelial cells), alveoli, bronchial cells, keratinocytes, and synovial cells.

It was also surprisingly observed that the length of the linker connecting the guanidino head group to the lipoamido moiety played a role in the transfection efficiency with chains of two or three carbon atom spacers between the amido function of the lipoamine and the guanidino head group giving higher transfection efficiencies than spacers of three or four carbon atom chains.

Table 1 shows the transfection efficiency of cationic lipids with an oleyl tail and a guanidino head group having linker chain lengths of 1 to 4 carbons in murine fibroblast (3T3) cells, epithelial cells (HBE) and vascular endothelial cells (IVEC). Transfection efficiencies are expressed relative to that observed for DOTMA™.

TABLE 1

| Compound | Linker length | 3T3 | HBE | IVEC |
| --- | --- | --- | --- | --- |
| 1B | 1 | 16.6 | 1.9 | 2.4 |
| 2B | 2 | 23.3 | 1.5 | 7.4 |
| 7B | 3 | 4.2 | 0.4 | 1.4 |
| 9B | 4 | 4.3 | 0.2 | 2.1 |

It was also surprisingly observed that substituents on the amino group of the guanidino head group also gave unexpectedly high transfection efficiencies. Table 2 shows the transfection efficiency of cationic lipids with an oleyl tail, an ethylene linker chain and varying substituents on the guanidino head group in murine fibroblast (3T3) cells, epithelial cells (HBE) and vascular endothelial cells (IVEC). Transfection efficiencies are expressed relative to that observed for DOTMA™.

TABLE 2

| Compound | 3T3 | HBE | IVEC |
| --- | --- | --- | --- |
| 2B | 16.6 | 1.9 | 7.4 |
| 2C | 9.0 | 1.5 | 7.3 |
| 2Q | 47.8 | 1.6 | 23.2 |
| 2O | 50.0 | 4.4 | 11.2 |
| 2R | 41.1 | 2.9 | 47.5 |

Transfection procedures may be carried out by direct injection into the cells of an animal in vivo. Alternatively, transfection may be carried out in vitro to cells explanted from the animal followed by reintroduction of the cells into the animal (ex vivo methods). Protocols for in vivo and ex vivo transfection in a clinical setting can be found in Human Gene Therapy, 7, 1621–1642 (1996). Tissues which may be transfected in vivo include airway epithelia and vascular endothelia.

Administration can be via any accepted systemic or local route, for example, via parenteral, oral (particularly for infant formulations), intravenous, nasal, bronchial inhalation (i.e., aerosol formulation), transdermal or topical routes, in the form of solid, semi-olid or liquid dosage forms, such as for example, tablets, suppositories, pills, capsules, powders, solutions, suspensions, aerosols, emulsions or the like, preferably in unit dosage forms suitable for simple administration of precise dosages. The compositions will include a conventional pharmaceutical carrier or excipient, a biologically active substance, a cationic lipid of Formula I and, in addition, may include other medicinal agents, pharmaceutical agents, carriers, adjuvants, etc. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical carriers include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "Remington's Pharmaceutical Sciences" by E. W. Martin.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The lipid-polyanion complexes of this invention are generally administered as a pharmaceutical composition comprising a pharmaceutical excipient in combination with a polyanion and a cationic lipid of Formula I. As described earlier, it will be particularly useful to deliver nucleic acids coding for therapeutically significant proteins. The level of the nucleic acid and cationic lipid in a formulation can vary within the full range employed by those skilled in the art. For in vitro administration, the nucleic acid can range from about 0.5 to 100 $\mu$M, preferably about 1.5 to 30 $\mu$M, and the cationic lipid can range from about 1 to 200 $\mu$M, preferably about 5 to 120 $\mu$M. For in vivo administration, the nucleic acid can range from about 0.1 to 10 mM, preferably about 0.2 to 2 mM, and the cationic lipid can range from about 0.1 to 20 mM, preferably about 0.2 to 10 mM.

Intravenous Administration

Intravenous injection has proven to be an important route of administration for therapeutic agents. Pharmaceutical formulations containing cationic lipids of the present invention can be administered via this route, for example, by preparing lipid complexes as described above and dispersal into an acceptable infusion fluid. A typical daily dose of a compound of the invention can be administered by one infusion, or by a series of infusions spaced over periodic intervals.

Controlled release liposomal liquid pharmaceutical formulations for injection or oral administration are described in U.S. Pat. No. 4,016,100. Liposomal applications for oral drug delivery of a lyophilized liposome/peptide drug mixture filled into intestine capsules have also been suggested, see U.S. Pat. No. 4,348,384. The foregoing are incorporated herein by reference.

Aerosol Administration

Aerosol administration is an effective means for delivering a therapeutic agent directly to the respiratory tract. Some of the advantages of this method are: 1) it circumvents the effects of enzymatic degradation, poor absorption from the gastrointestinal tract, or loss of the therapeutic agent to the hepatic first-pass effect; 2) it administers therapeutic agents which would otherwise fail to reach their target sites in the respiratory tract due to their molecular size, charge or affinity to extra-pulmonary sites; 3) it provides for fast absorption into the body via the alveoli of the lungs; and 4) it avoids exposing other organ systems to the therapeutic agent, which is important where exposure might cause undesirable side effects. For these reasons, aerosol administration is particularly advantageous for treatment of asthma, local infections of the lung, and other diseases or disease conditions of the lung and respiratory tract.

There are three types of pharmaceutical inhalation devices, nebulizers inhalers, metered-dose inhalers (MDI) and dry powder inhalers (DPI). Nebulizer devices produce a stream of high velocity air that causes the therapeutic agent (which has been formulated in a liquid form) to spray as a mist which is carried into the patient's respiratory tract. MDIs typically have the formulation packaged with a compressed gas. Upon actuation, the device discharges a measure amount of therapeutic agent by compressed gas, thus affording a reliable method of administering a set amount of agent. Historically, MDIs have used chlorofluorocarbons (CFC) as the compressed gas to propel the therapeutic agent. In recent years, CFCs have been linked with the depletion of the earth's ozone layer. As a result of this, alternative propellants that are non-ozone threatening are being sought out as potential replacements for CFCs.

DPIs administer therapeutic agents in the form of a free flowing powder that can be dispersed in the patient's inspiratory air-stream during breathing by the device. In order to achieve a free flowing powder, the therapeutic agent is formulated with an excipient, such as lactose. A measured amount of the therapeutic is stored in a capsule form and is dispensed to with each actuation. Examples of DPIs being used are Spinhaler® (for the administration of disodium cromoglycate), Rotahaler® (for albuterol) and Turbuhaler® (for terbutaline sulfate). All of the above methods can be used for administering the present invention, particularly for the treatment of asthma and other similar or related respiratory tract disorders.

Suppositories

For systemic administration via suppository, traditional binders and carriers include, for example, polyalkylene glycols or triglycerides [e.g., PEG 1000 (96%) and PEG 4000 (4%)]. Such suppositories may be formed from mixtures containing active ingredients in the range of from about 0.5 wt/wt % to about 10 wt/wt %; preferably from about 1 wt/wt % to about 2 wt/wt %.

Liquids

Liquid pharmaceutically administrable compositions can, for example, be prepared by dissolving, dispersing, etc. an active compound (about 0.5% to about 20%), as described above, and optional pharmaceutical adjuvants in a carrier, such as, for example, water, saline, aqueous dextrose, glycerol, ethanol and the like, to thereby form a solution or suspension.

Actual methods of preparing such dosage forms are known, or will be apparent, to those skilled in this art; for example, see *Remington's Pharmaceutical Sciences*, Mack Publishing Company, Easton, Pa., 16th Ed., 1980. The composition to be administered will, in any event, contain a quantity of the active compound(s) in a pharmaceutically effective amount for relief of the particular condition being treated in accordance with the teachings of this invention.

EXAMPLES

The following examples are given to enable those skilled in the art to more clearly understand and to practice the present invention. They should not be considered as limiting the scope of the invention, but merely as being illustrative and representative thereof.

Abbreviations:

BOC—tertbutyloxycarbonyl
CDI—carbonyldiimidazole
thio-CDI—thiocarbonyldiimidazole
PYBOP—(benzotriazol-1-yloxy)tripyrrolidino-phosphonium hexafluorophosphate
DIEA—di-isopropylethylamine Example 1

Preparation of Compounds of Formula I

A. Preparation of 3-[N',N"-bis(2-tertbutyloxycarbonylaminoethyl)guanidino]-N,N-dioctadec-9-enylpropionamide (Compound 20 with reference to FIGS. 1 and 2)

The specific reaction sequence for the synthesis of 2B is shown in Reaction Schemes C and D. Intermediates described in the experimental procedure given below are numbered as shown in these Reaction Schemes.

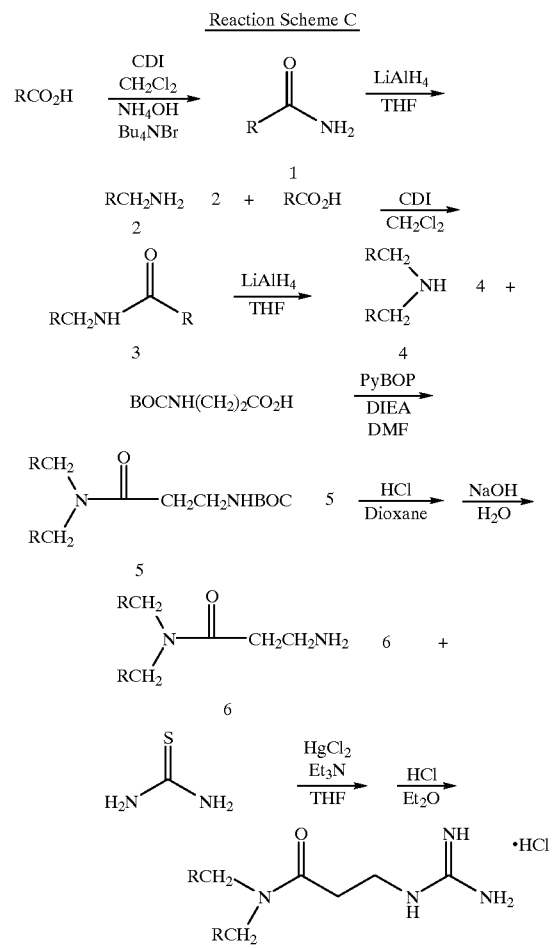

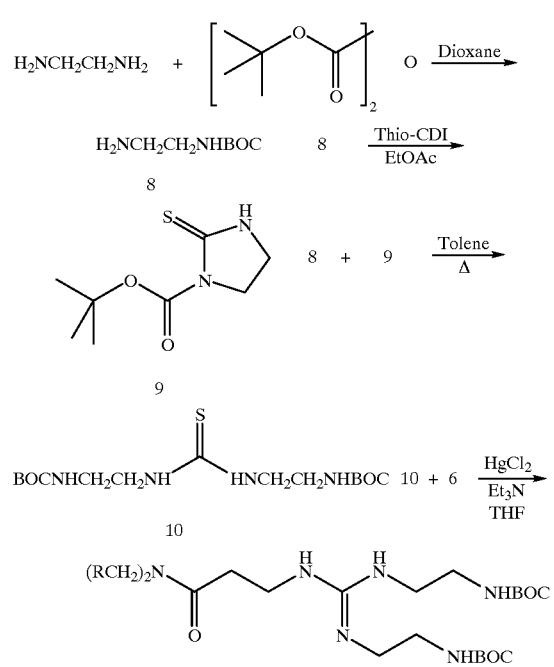

Compound 1

To a room temperature solution of oleic acid (99+%, 12.48 gm., 44.2 mmol) in methylene chloride (200 ml) was added 1,1'- carbonyldiimidazole (8.24 g, 50.2 mmol). After stirring 30 minutes, concentrated ammonium hydroxide (50 ml) and tetrabutylammonium bromide (1.42 g, 4.42 mmol) was added and the resulting mixture was rapidly stirred for 2 hours. After stirring with water (100 ml), the organic layer was separated, washed two times with water, dried (magnesium sulfate), and stripped in vacuo. The crude product (12.88 g) was recrystallized from hexane to give 12.35 g of compound 1 as a white solid.

$^1$H NMR (CDCl$_3$) δ 0.86 (t, J=6.6 Hz, 3H), 1.27–1.80 (m, 22H), 2.0 (m, 4H), 2.22 (t, J=8.0, 2H), 5.30 (m, 2H); MS m/z 281 (M+).

Compound 2

To a room temperature solution of compound 1 (10 g, 35.5 mmol) in dry tetrahydrofuran (100 ml) under argon was added dropwise over one minute via syringe lithium aluminum hydride (39 ml, 39 mmol one molar in THF). There was a slight exotherm. The milky mixture was stirred one hour at room temperature and then at 50° C. for six hours. To the rapidly stirred ice cooled mixture was added cautiously dropwise water (1.5 ml), followed by aqueous sodium hydroxide (15%, 1.5 ml), and then water (3.5 ml). The resulting white granular solid was filtered and washed with methylene chloride (30 ml). After stripping the methylene chloride solution, the resulting co or less liquid (9.7 g) was flash chromatographed on silica gel (eluting from 5% to 7% to 10% methanol in methylene chloride) to give 7.4 g colorless liquid.

$^1$H NMR (CDCl$_3$) δ 0.88 (t, J=6.6 Hz, 3H), 1.27–1.64 (m, 36H), 2.00 (m, 4H), 2.68 (t, J=7.0 Hz, 2H), 5.36 (m, 2H); MS m/z 267 (M+).

Compound 3

To a room temperature solution of oleic acid (99%, 28.25 g, 100 mmol) in methlene chloride (400 ml) was added at once 1,1'-carbonyldiimidazole (17.84 g, 110 mmol) and stirred under argon 30 minutes. Compound 2 (26.75 g, 100 mmol) was added and stirred under argon an additional two hours. Water (200 ml) was added and the mixture stirred a few minutes. The methylene chloride layer was separated, dried (magnesium sulfate), and concentrated in vacuo to provide a white grease (57.5 g).

$^1$NMR (CDCl$_3$) δ 0.88 (t, J=6.5 Hz, 6H), 1.27–1.73 (m, 54H), 2.01 (m , 8H), 2.15 (t, J=6.0 Hz, 2H), 3.26 (q, J=7.0 Hz, 2H), 5.35 (m, 2H); MS m/z 531 (M+).

Compound 4

To a room temperature solution of compound 3 (9.67 g, 18.25 mmol) in dry tetrahydrofuran (100 ml) under argon was added dropwise over one minute via syringe lithium aluminum hydride (20 ml, 20 mmol one molar in THF) and then stirred under argon at 60° C. overnight. To the rapidly stirred ice cooled mixture was added cautiously dropwise water (0.7 ml), followed by aqueous sodium hydroxide (15%, 0.7 ml), and then water (2.1 ml). The resulting white granular solid was filtered and washed with ether (50 ml), dried (anhydrous magnesium sulfate), and concentrated in vacuo. The crude yellow oil (9.45 g) was flash chromatographed over silica gel (25% ethyl acetate/hexanes plus 1% triethylamine) furnishing 4.2 g of a pale yellow oil and 0.89 g of slightly impure product.

$^1$H NMR (CDCl$_3$) δ 0.88 (t, J=2.6 Hz, 6H), 1.25–1.98 (m, 46H), 2.02 (m, 8H), 2.58 (t, J=2.5 Hz, 4H), 5.34 (m, 4H); MS m/z 518 (M+).

Compound 5

To a room temperature mixture of compound 4 (10.36 g, 20 mmol), N-t-BOC-β-alanine (3.78 g, 20 mmol), and PyBOP (12.49 g, 24 mmol) under argon was added dimethyformamide (75 ml) and was stirred for five minutes. To the solution was added diisopropylethylamine (10.45 ml, 60 mmol) followed by stirring an additional 45 minutes. To the stirring brown solution was added water (500 ml) and ethyl acetate (250 ml). The organic layer was separated and the aqueous layer is extracted twice with ethyl acetate (100 ml). The combined organic portions were washed with water (100 ml), dried (magnesium sulfate), and concentrated in vacuo. The crude brown oily solid was flash chromatographed over silica gel (5% to 10% ethyl acetate/hexanes) to give 13.45 g of a colorless oil.

$^1$H NMR (CDCl$_3$) δ 0.88 (t, J=6.7 Hz, 6H), 1.26–1.42 (m, 45H), 1.42 (s, 9H), 1.43–1.75 (m, 6H), 2.00 (m, 8H), 2.50 (t, J=4.8, 2H), 3.16 (br t, 2H), 3.30 (br t, 2H), 3.41 (br t, 2H), 5.35 (m, 2H); MS m/z 688 (M+).

Compound 6

To a solution of compound 5 (7.75 g, 11.2 mmol) in dry dioxane (20 ml) under argon was added 4N HCl in dioxane (25 ml) and stirred at room temperature for overnight. The solution was stripped, acetonitrile (50 ml) was added, stripped, and repeated twice more. The residue was stirred with ethyl acetate (200 ml) and 10% aqueous sodium hydroxide solution (100 ml) for two hours. The ethyl acetate layer was separated, the aqueous layer was extracted with ethyl acetate (50 ml), the combined ethyl acetate portions were dried (magnesium sulfate), and concentrated in vacuo. The crude oil (6.6 g) was flash chromatographed over silica gel (3% then 10% methanol/methylene chloride ) to yield 6.29 g of a very pale yellow oil.

$^1$H NMR (CDCl$_3$) δ 0.88 (t, J=7.0 Hz, 6H), 1.27–1.60 (m, 54H), 2.01 (m, 8H), 2.55 (t, J=5.9 Hz, 2H), 2.95 (m, 2H), 3.10 (br t, 2H), 3.15 (br t, 2H), 3.25 (br t, 2H), 5.34 (m, 4H); MS m/z 589 (M+).

Compound 7

To a 65° C. solution of compound 6 (0.589 g, 1.0 mmol), thiourea (95 mg, 1.25 mmol), triethylamine (0.42 ml, 3.0 mmol), and tetrahydrofuran (25 ml) was added mercuric chloride (0.34 g, 1.25 mmol) and stirred at 65° C. under argon for seven days. The white suspension gradually turned black. The suspension was cooled to room temperature, filtered through celite, and the solution was stripped. The crude dense oil was flash chromatographed over silica gel (5% to 8% to 10% to 15% methanol/methylene chloride plus 1% conc. ammonium hydroxide). Starting material (425 mg) was recovered and pure product (170 mg) as a pale yellow oil was obtained. The oil was dissolved in 10% methanol/ methylene chloride and 1N HCl in ether (1 ml) was added and stripped to give a cloudy grease.

$^1$H NMR (CDCl$_3$) δ 0.88 (t, J=6.5 Hz, 6H), 1.27–1.78 (m, 60H), 2.00 (m, 8H), 2.56 (m, 2H), 3.18 (m, 2H), 3.28 (br t, 2H), 3.54 (br t, 2H), 5.34 (m, 4H), 8.29 (br t, 1H); MS m/z 630(M+).

Compound 8

To a room temperature solution of ethylene diamine (21 g, 0.349 moles) in dry dioxane (120 ml) was added dropwise over 3 hours di-t-butyl-dicarbonate (9.8 g, 26.6 mmol) in dioxane (120 ml). The cloudy mixture gradually clears. The mixture was stirred overnight at room temperature. After stripping, the residue was stirred with water (200 ml) and the white precipitate was filtered. The filtrate was extracted with methylene chloride (200 ml) three times, dried (magnesium chloride), and stripped giving a colorless oil (4.8 g).

$^1$H NMR (CDCl$_3$) δ 1.44 (s, 9H), 2.83 (t, J=6 Hz, 2H), 3.17 (q, J=6 Hz).

Compound 9

To a room temperature mixture of compound 8 (0.8 g, 5 mmol) and ethyl acetate (35 ml) was added 1,1'-thiocarbonyldiimidazole (1.07 g, 6 mmol) and stirred overnight. After stripping, the residue was flash chromatographed over silica gel with 30% to 50% ethyl acetate/ hexane to give 0.66 g solid.

$^1$H NMR (CDCl$_3$) δ 1.53(s, 9H), 3.59 (t, J=8.4 Hz, 2H), 4.10 (t, J=7 Hz, 2H).

Compound 10

A solution of compound 8 (0.275 g, 1.72 mmol), compound 9 (0.347 g, 1.72 mmol), and toluene (4 ml) was stirred at 75 degrees under argon overnight. After stripping, the residue was flash chromatographed over silica gel with 2% to 3% methanol/methylene chloride) to give an oil (0.37 g).

$^1$H NMR (CDCl$_3$) δ 1.45 (s, 9H), 3.34 (t, J=5.8 Hz, 2H), 3.54 (m, 2H).

Compound 11

To a 65° C. solution of compound 6 (0.29 g, 0.494 mmol), compound 10 (0.21 g, 0.596 mmol), triethylamine (0.27 ml, 1.98 mmol), and tetrahydrofuran (25 ml) was added mercuric chloride (0.16 g, 0.596 mmol) and stirred at 65° C.

under argon for one day. The white suspension gradually turned black. The suspension was filtered through celite, and the solution was stripped. The crude dense oil was flash chromatographed over silica gel (5% to 10% methanol/ methylene chloride plus 1% conc ammonium hydroxide) to give a dense oil (0.21 g).

$^1$H NMR (CDCl$_3$) δ 0.88 (t, J=6.8 Hz, 6H), 1.2–1.6 (m, 72H), 2.1 (m, 10H), 2.78 (m, 2H), 3.2–3.55 (m, 14H), 3.68 (m, 2H), 5.35 (m, 4H); MS m/z 916 (M+).

B. Preparation of other Compounds of Formula I

Using the procedures described above and substituting the appropriate acid for oleic acid and the appropriate thiourea or isothiouronium salt for 10, the compounds listed below were also prepared. The compounds are defined with reference to the lipoamido tail groups and the cationic head groups as shown in FIGS. 1 and 2. For example, compound 1A refers to the compound 1 shown in FIG. 1 in which X is the head group A of FIG. 2

Gene Therapy Novel Lipids

| CPD # | MP ° C. | MS (M + H) |
|---|---|---|
| 1A |  | 575 m+ |
| 1B | 76.3–78.8 | 617.3 |
| 1C |  | 673.9 |
| 1D |  | 781.8 |
| 1E |  | 617.7 m+ |
| 2A |  | 589.5 |
| 2B |  | 631.4 |
| 2C |  | 687.6 |
| 2D |  | 795.5 |
| 2E |  | 631.6 m+ |
| 2F |  | 831.8 |
| 2G |  | 673.6 |
| 2H | 102–105.1 | 763.6 |
| 2I |  | 703.6 |
| 2J |  | 779.6 |
| 2K |  | 670 m+ |
| 2M |  | 741.5 |
| 2O |  | 916.8 |
| 2P |  | 717.7 |
| 2Q |  | 743.6 |
| 2R |  | 945.7 |
| 2S |  | 832.7 |
| 2T |  | 973.8 |
| 2U |  | 799.8 |
| 3A |  | 579.4 |
| 3B | 88.8–91.2 | 621.6 |
| 3C |  | 677.7 |
| 3D |  | 785.7 |
| 3E | 65.9–67.8 | 621.5 m+ |
| 4A | 27.3–29.0 | 592 m+ |
| 4B | 54.5–57.0 | 635.7 |
| 4C |  | 691.7 |
| 4D |  | 799.7 |
| 4E | 166.4–168.4 | 635.8 m+ |
| 5A |  | 410 m+ |
| 5B | 91.2–92.5 | 453.4 |
| 5D |  | 617.5 |
| 5E | 49–56 | 453.6 m+ |
| 6A |  | 424 m+ |
| 6B |  | 467.7 |
| 6D |  | 631.4 |
| 6E | 125–129.2 | 467.5 m+ |
| 7A |  | 603.6 |
| 7B | 66.5–69.6 | 645.6 |
| 8A |  | 439.4 |
| 8B |  | 481.4 |
| 8R |  | 781.5 |
| 9B |  | 659.6 |
| 10B |  | 495.5 |
| 11B |  | 623.7 |
| 11N |  | 723.5 |
| 12B |  | 745.6 |
| 12N |  | 845.5 |
| 13B |  | 523.6 |
| 14B | 141.5–154 | 578.6 |

Example 2

Preparation of Liposomes

In the following examples, cationic liposome vesicles containing a 1:1 molar ratio of the indicated cationic lipid and the neutral lipid dioleoyl-phosphotidylethanolamine (DOPE) were used.

For example, 9.19 mg. of 2-guanidino-N,N-di-octadec-9-enyl-propionamide (compound 2B) dissolved in methylene chloride was mixed with 10.81 mg DOPE in chloroform. The solvents were removed by rotary evaporation, and the lipid film was dried under vacuum. The films were rehydrated with 20 ml sterile water to a concentration of 1 mg/ml, warmed to 45° C., and sonicated in high power bath sonicator or extruded to form multilamellar liposome vesicles. Particles were sized by laser light scattering using Coulter Submicron Particle Sizer. N4M, (Coulter, Hialeah Fla.). The average particle size of novel liposome preparations was 296 nm±40.

Example 3

Preparation of Lipid-Nucleic Acid Complexes

In the following examples, the PCMVβ plasmid (Clontech, Palo Alto, Calif.), encoding the lacZ/β-galactosidase gene was stored at −20° C. in water at a concentration of 1 mg/ml. Complexes for in vivo delivery were made with the pCT0129 plasmid encoding the CAT gene linked to the CMV promoter. Plasmid DNA was diluted in serum-free Optimem media (LifeTechnologies, Gathersburg, Md.) to a concentration of 8 ug/ml, and was added to an equal volume of cationic liposomal solution. Complexes were formed for 30–45 minutes prior to use in transfection experiments. Complexes were prepared with lipid/DNA ratios of 1:1, 1:5, and 1:25 by weight.

Lipid/DNA complexes were also prepared using two commercially available lipid transfection agents, Lipofectamine™ and Lipofectin™ (LifeTechnologies, Gathersburg, Md.). These agents were employed to assess the transfection efficiency relative to commercially available lipids routinely used for transfection.

Example 4

Determination of Transfection Efficiencies

The transfection efficiencies obtained using guanidino-containing liposomes of the present invention relative to that of liposomes containing quaternary amines were compared in media containing or lacking serum (FIGS. 3–5). The effect of varying the co-lipid (DOPE or cholesterol) as well as the molar ratio of co-lipid to cationic guanidino-lipid on transfection efficiency was also determined (FIG. 6). Comparison data of the transfection efficiency of lipids of the present invention to that of DOTMA™ and GS2888 were also determined both in vitro (FIG. 7) and in vivo (FIG. 8).

Novel lipid/DNA complexes were routinely screened in a 96-well microtitre format to determine the efficiency of gene transfer using three different cell lines, NIH3T3 murine fibroblasts (ATCC # CTRL 1658), IVEC human endothelial cells (purchased from Dr. Denise Paulin, Pasteur Institute, Paris, France, *J.Cellular Physiol.*, 457, 41–51 (1993), and 16-HBE14o-human epithelial cells, *Am. J. Physiol.*, 268, L347–L360 (1995).

Cells were cultured in CoStar microtitre wells (Cambridge, Mass.) coated with 0.5% collagen (Collaborative Biomedical, Bedford, Mass.). Cells were seeded at 20,000 cells/well in complete culture media 48 hours prior to transfection. On the day of transfection, media was aspirated, cells were washed 3 times with Optimem medium, 50 μl of Optimem media with or without 10% FBS (BioWhittaker, Walker) was added to each microtitre well and 50 μl of lipid/DNA complex was added to appropriate wells, to yield a final DNA concentration of the cells were incubated with the lipid DNA complex for 5 hours at 37° C. The media was then aspirated, replaced with 100 μl of complete serum containing culture media, and the cells were then cultured for an additional 48 hours.

To assess transfection efficiency, cell lysates were prepared, and β-galactosidase activity was determined using the fluorogenic substrate, 4-methyl umbelliferyl β-D galactosidase (MUG) (Sigma, St. Louis, Mo.) according to the manufacturers instructions. The amount of substrate hydrolyzed was measured fluorometrically using a CytoFluorII flurometer (Millipore, Bedford Mass.). Total cellular protein in the lysates was determined using BCA assay (Pierce, Rockford Ill.). The data is presented as fluorescence units/μg protein and each data point represents the average of three sample measurements.

A. Transfection of Human Endothelial Cells (IVEC)

IVEC cells (2×10$^4$) were transfected with 2 μg/ml pCMV-β plasmid DNA complexed with 0, 2, 10, or 50 μg/ml cationic liposomes in serum-free (FIG. 3A) or serum-containing medium (FIG. 3B). 48 hours post transfection β-galactosidase activity was measured using the fluorescent substrate (MUG) and activity was normalized per μg protein in cell lysate. Each data point represents the average from triplicate samples. In the presence of serum, as illustrated in FIG. 3B, several of the novel compounds transfect at an efficiency of 2 to 10 times better than the commercially available compound.

B. Transfection of Human Bronchial Epithelial Cells (16HBE)

16HBE cells (2×10$^4$) were transfected with 2 μg/ml pCMV-β plasmid DNA complexed with 0, 2, 10, or 50 μg/ml cationic liposomes in serum-free (FIG. 4A) or serum-containing medium (FIG. 4B). 48 hours post transfection β-galactosidase activity was measured using the fluorescent substrate (MUG) and activity was normalized per μg protein in cell lysate. Each data point represents the average from triplicate samples.

The data in FIG. 4A shows that in human bronchial epithelial cells, in the absence of serum, several of the novel compounds transfect at an efficacy rate comparable to the commercially available compound, Lipofectin™, and one of the novel compounds transfects with approximately 30% more efficiency. Furthermore, in the presence of serum, as illustrated in FIG. 4B, several of the novel compounds transfect with efficiencies approximately several times better than the commercially available compound.

C. Transfection of Murine 3T3 Fibroblast Cells

3T3 fibroblasts (2×10$^4$) were transfected with 2 μg/ml pCMV-β plasmid DNA complexed with 0, 2, 10, or 50 μg/ml cationic liposomes in serum-free, (FIG. 5A) or serum-containing medium (FIG. 5B). 48 hours post transfection β-galactosidase activity was measured using the fluorescent substrate (MUG) and activity was normalized per μg protein in cell lysate. Each data point represents the average from triplicate samples.

The data in FIG. 5A shows that in murine 3T3 fibroblast cells, in the absence of serum, several of the novel compounds transfect with approximately 30 to 50% more efficacy than the commercially available compound, Lipofectin, shown on the far right of the graph. Additionally, in the presence of serum, as illustrated in FIG. 5B, several of the novel compounds transfect at efficiencies of 4 to 10 times better than the commercially available compound.

D. Effect of Co-Lipids on the Transfection Efficiency of the Novel Compound, 2-guanidino-N,N-di-octadec-9-enyl-propionamide (2B) in Human Endothelial Cells Cationic liposomes were prepared containing 2B: cholesterol:DOPE at various molar ratios. IVEC cells (2×10$^4$) were transfected with 2 μg/ml pCMV-β plasmid DNA complexed with 0, 2, 10, or 50 μg/ml cationic liposomes in serum or serum-free medium (FIG. 6). 48 hours post transfection β-galactosidase activity was measured using the fluorescent substrate (MUG) and activity was normalized per μg protein in cell lysate. Each data point represents the average from triplicate samples.

The data in FIG. 6 shows that in human endothelial cells, in the presence of serum, the novel compound 2B combined with cholesterol and DOPE at the ratios of 1:0:1 and 0.5:0.25:0.25 transfects with approximately 10 to 20 times more efficacy than the commercially available compounds, Lipofectin™ and LipofectAmine™, shown on the far left of the graph. In the absence of serum, as illustrated in FIG. 6, the novel compound 2B combined with DOPE at the ratio of 1:1 transfects at an efficiency of approximately 40% better than the commercially available compound, LipofectAmine™.

E. Transfection Activity of the Novel RS-Compounds Relative to Cytofectin GS2888

The BOC protected GS-2888 was prepared in two ways, as a chloride salt and as a free base. The lipid ratio of cationic to neutral lipid was 1:1. FIG. 7B serves as a control exhibiting that GS-2888 was active. The compounds used in both FIGS. 7A and 7B were prepared from the same batch, on the same day, using the same DNA on different cells.

2×10$^4$ cells were transfected with 2 μg/ml pCMV-β plasmid DNA complexed with 0, 2, 10, or 50 μg/ml cationic liposomes in serum-containing medium (FIG. 4B) . GS-2888 was formulated with neutral lipid at 1:1 and 2:1 molar ratios. 48 hours post transfection β-galactosidase activity was measured using the fluorescent substrate (MUG) and activity was normalized per μg protein in cell lysate. Each data point represents the average from triplicate samples. FIG. 7A illustrates transfection efficacy in IVEC endothelial cells; FIG. 7B illustrates transfection efficacy in 16-HBE epithelial cells. FIG. 7A shows that in HBE cells several of the novel guanidino lipids are 10-fold more efficient than GS2888.

F. In Vivo Transfection Efficiency of Novel Compounds of This Invention

A reproducible process for preparing DNA/lipid complexes at concentrations and volumes suitable for in vivo delivery was established. This process was developed with liposomes that contained the cationic lipid DOTMA™ or cationic lipids of the present invention formulated with the neutral lipid DOPE. DNA was in the form of polyanionic circular plasmids. Successful complexation was achieved by the slow infusion of the minor component into a rapidly stirred solution of the predominant component. This process was employed in a sterile environment and was shown to be reproducible with respect to complex size over a broad range of concentrations (DNA 0.15–1.5 mM; lipid 0.2–8.5 mM) and charge ratios.

In vivo testing was performed by intratracheal installation of lipid/DNA complexes in anesthetized rats. A plasmid (pCT0129) encoding the chloramphenicol acetyl transferase gene (CAT) linked to a CMV promoter was utilized for all in vivo assessments of transfection efficiency. Transfection complexes typically contained 200 μg DNA complexed with 0.8–3.5 mM liposomes and 5% dextrose. 250 μl of complex was delivered to rat lungs by installation through P10 tubing connected to a 30 gauge needle. Animals were sacrificed 40 hours later, the lungs were harvested and analyzed for enzyme activity using CAT Elisa assay (Boehringer Mannheim).

The results are shown in FIG. 8 for different sets of cationic lipids compared to DOTMA™. Data are expressed as the average pg CAT protein/mg lung protein (n=8) and show that the levels of CAT protein detected in animals receiving DNA complexed with lipids of the invention were 50 fold higher than that detected in animals receiving DOTMA™-complexed DNA.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound of Formula I

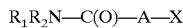 Formula I wherein:

$R_1$ and $R_2$, which may be the same or different, are $C_{10}$–$C_{26}$ hydrocarbyl groups;

A is a alkylene group wherein one or more methylene groups is optionally replaced by a group Y (provided that none of the Y groups are adjacent to each other), where each Y is independently in the direction shown, —O—, —OC(O)—, —C(O)O—, —NR$_5$—, —NR$_5$C(O)—, —C(O)NR$_5$—, NR$_5$C(O)NR$_5$—, —NR$_5$C(O)O—, —OC(O)NR$_5$—, —S(O)$_n$— (where n is 0, 1 or 2) or —NZ—C(=NZ)NZ—, wherein each Z is independently H or —(CH$_2$)$_m$NR$_5$—C(=NR$_5$)NR$_5$ with m being an integer from 1–10, and each R$_5$ is independently H or lower alkyl;

X is: a —NH—C(=NR$_3$)NHR$_4$, wherein R$_3$ and R$_4$ are independently hydrocarbyl, haloalkyl, hydroxyalkyl, O-protected hydroxyalkyl, alkoxyalkyl, haloalkoxyalkyl, aryloxyalkyl, aminoalkyl, mono- or di-substituted aminoalkyl, N-protected-aminoalkyl, acyl, alkoxycarbonyl, aryloxycarbonyl, —C(O)NR$_6$R$_7$ (where R$_6$ and R$_7$ are independently H or hydrocarbyl) or a nitrogen protecting group;

provided that:

when $R_1$ and $R_2$ are both identical $C_{16}$ alkyl groups, A is not a butylene chain;

and salts, solvates, resolved and unresolved enantiomers, diastereomers and mixtures thereof.

2. The compound of claim 1, wherein X is —NH—C(=NR$_3$)NHR$_4$.

3. The compound of claim 1, wherein $R_1$ and $R_2$ are monounsaturated alkenyl groups.

4. The compound of claim 1, wherein $R_1$ and $R_2$ are alkyl groups.

5. The compound of claim 2, wherein $R_1$ and $R_2$ are identical.

6. The compound of claim 5, wherein $R_1$ and $R_2$ are CH$_3$(CH$_2$)$_7$CH=CH(CH$_2$)$_8$—.

7. The compound of claim 2 wherein A is a methylene or ethylene group, and R$_3$ and R$_4$ are N-protected-aminoalkyl.

8. The compound of claim 7, wherein R$_3$ and R$_4$ are N-protected aminoalkyl groups selected from the group consisting of 2-(t-butyloxycarbonylamino)ethyl and 3-(t-butyloxycarbonyl)propyl.

9. The compound of claim 8, wherein $R_1$ and $R_2$ are monounsaturated alkenyl groups.

10. The compound of claim 9, wherein $R_1$ and $R_2$ are identical.

11. The compound of claim 10, wherein $R_1$ and $R_2$ are CH$_3$(CH$_2$)$_7$CH=CH(CH$_2$)$_8$—.

12. A pharmaceutical formulation comprising a compound of claim 1, and pharmaceutically acceptable excipients.

* * * * *